US005888501A

United States Patent [19]

Backman et al.

[11] Patent Number: 5,888,501

[45] Date of Patent: Mar. 30, 1999

[54] INDUCED SYSTEMIC RESISTANCE OF PLANTS TO PATHOGENIC MICROORGANISMS

[75] Inventors: Paul A. Backman; Sadik Tuzun, both of Auburn, Ala.

[73] Assignee: Auburn University, Auburn University, Ala.

[21] Appl. No.: 280,727

[22] Filed: Jul. 26, 1994

[51] Int. Cl.[6] .................................................... A01N 63/00

[52] U.S. Cl. ...................... 434/93.4; 424/93.3; 424/93.5; 424/93.51

[58] Field of Search .................................. 424/930, 93.3, 424/93.5, 93.51, 93.4

[56] References Cited

U.S. PATENT DOCUMENTS

| | | | |
|---|---|---|---|
| 5,041,384 | 8/1991 | Wilson et al. | 435/255 |
| 5,288,488 | 2/1994 | Backman et al. | 424/93 D |

OTHER PUBLICATIONS

Adams, A.J., Fenlon, J.S., and Palmer, A. 1988. Improving the biological efficacy of small droplets of permethrin by the addition of silicon–based surfactants. Ann. Appl. Boil. 122:19–31.

Aitken–Christie, J., and Coker, A. 1986. Surfactants aid uptake of cytokinin and area into juvenile *Pinus radiata* plantlets. Int. Plant Propagators. Soc. Combined Proc. 36:499–506.

Buick, et al 1993. The Role of surface Tension of Spreading Droplets in Absorption of a Herbicide Formulation via Leaf Stomata. Pestic Sci. 38:227–235.

Dean, R.A., and J. Kuc, 1985. Induced systemic protection in plants. Trends in Biotechnology 3:125–129.

Field, R.J. and Bishop, N.G. 1988. Promotion of stomatal infiltration of glyphosate by an organosilicone surfactant reduces the critical rainfall period. Pestic. Sci. 24:55–62.

Greenberg, J. Monselise, S.P., and Goldschmidt, E.E. 1987. Improvement of gibberellin efficiency in proloning the citrus harvest season by the surfactant L–77. J. Am. Soc. Hort. Sci. J. 112:625–629.

Hildebrand, P.D. 1989. Surfactant–like characteristics and identity of bacteria associated with broccoli head rot in Atlantic Canada. Can J. Plant pathol. 11:205–214.

Kirkwood, Ralph C. 1993. Use of Mode of Action of Adjuvants for Herbicides: A Review of some Current Work. Pestic. Sci. 38:93–102.

Neumann, P.M., and Prinz, R. 1974. Evaluation of surfactants for use in the spray treatment of iron chlorosis in citrus tree. J. Sci. Food Agric. 25:221–226.

Roggenbuck, et al. 1993. Study of Enhancement of Herbicide Activity and Rainfastness by an Organosilicone Adjuvant Utilizing Radiolabelled Herbicide and Adjuvant. Pestic. Sci. 37:121–125.

Singh, Megh. 1993. Effect of Organosilicon–Based Adjuvants on Herbicide Efficacy. Pestic. Sci. 38:219–225.

Stevens, Peter J.G. 1993. Organosilicone Surfactants as Adjuvants for Agrochemicals. Pestic. Sci. 38:103–122.

Stock, David. 1993. Possible Mechanisms for Surfactants–Induced Foliar Uptake of Agrochemicals. Pestic. Sci. 38:165–177.

Tuzun, S. and Kuc, J. 1991. Plant Immunization: An Alternative to Pesticides for Control of Plant Diseases in the Greenhouse and Field. Food and Fertilizer Technology Center, Technical Bulletin, No. 124.

Wei, G. Kloepper, J.W., and Tuzun S. 1991. Induction of systemic resistance of cucumber to Colletotrichum orbiculare by select strains of plant growth–promoting rhizobacteria. Phytopathology 81:1508–1512.

Wills, Gene D. Hanks, James E. and Mack, Robert E. 1993. Evaluation of the Effect of a Paraffinic Petroleum Oil–based Adjuvant and an Organo–silicone–Modified . . . etc. Pestic. Sci. 280–282.

Zidak, N.K., P.A. Backman, and J.J. Shaw, 1992, Promotion of bacterial infection of leaves by an organosilicone surfactant: Implications for biological weed control. Biological Control 2:111–117.

*Primary Examiner*—Herbert J. Lilling
*Attorney, Agent, or Firm*—Weiser & Associates, P.C.

[57] ABSTRACT

A formulation which induces systemic immunity in plants which comprise a surfactant which reduces the surface tension to below about 30 dynes/cm and the contact angle of liquids on the surface to zero. The plants which have been immunized and a method of applying the formulation to induce such immunity to the plants.

50 Claims, 20 Drawing Sheets

INDUCED SYSTEMIC RESISTANCE OF PLANTS TO PATHOGENIC MICROORGANISMS

FIELD OF THE INVENTION

This invention relates to the field of inducing immunity in plants. More specifically, this invention relates to inducing resistance of plants to disease by introduction of microorganisms into the plant.

BACKGROUND

This invention relates to the world-wide problem of hunger and of increasing yields of crops to feed an ever increasing human and food animal population. This invention also relates to the problem of controlling diseases in plants. A large proportion of the world's food supply is lost every year due to plant diseases which reduce food yields by killing plants, reducing numbers of fruits and vegetables from infected plants, and by retarding the growth of crop plants.

Classically, attempts to control diseases in plants consisted of coating plant surfaces with toxic substances which prevented pathogens, primarily fungi and bacteria, from entering the plant through direct penetration and/or through natural openings such as stomata. Later, systemic chemical fungicides were developed which killed fungi upon infection of the plant.

Many of these chemicals used in plant disease control, however, are enviromentally damaging. Since these chemical control methods require the application of toxic substances to plants, these chemicals find their way into human and animal food and pollute waterways, often causing pathology to fish, birds, and other wildlife. Additionally, many chemicals are toxic for only a limited range of pathogens, requiring the application of multiple chemicals in order to achieve broad protection. Chemicals may also have to be reapplied during a growing season if the chemicals are washed off the plants during a rain.

A second method of controlling pathogens is through the use of disease resistant cultivars of plants. This method has not proven to be totally satisfactory because disease resistant cultivars may not produce the highest yield or highest quality crop compared to non-resistant ones. Also, because many pathogens exist as distinct strains, a cultivar which is resistant to one strain of a pathogen may not be resistant to a different strain.

Recently, researchers have determined that plants have a system for disease resistance whereby systemic acquired resistance can be induced. Induced Systemic Resistance ("ISR") has been induced by prior inoculation with pathogens, nonpathogens and microbial metabolites.

ISR has been induced in a great many plant species, including cereals such as barley, corn, oat, rice, and wheat, cucurbits such as cucumber, muskmelon, and watermelon, legumes such as bean, cowpea, pea, and soybean, solanaceous plants such as pepper, potato, tobacco, and tomato, fruits such as pear, grape, peach, plum, strawberry, and apple, and other plants such as beet, cotton, coffee, radish, carnation and Douglas fir, to protect the plants from a variety of leaf and root pathogens. ISR is reported to be a broad, non-specific form of immunity whereby induction of immunity to one pathogen, for example a bacteria, may result in immunity to a great variety of pathogens, such as other bacteria, viruses, and fungi.

ISR is reported to be mediated by activation of multiple mechanisms for disease resistance. One such mechanism is the accumulation of low-molecular weight antimicrobial substances (phytoalexins) at and immediately around sites of infection. Phytoalexins accumulate rapidly after infection or stress in plants sensitized to respond by prior infection.

Other components of the ISR complex include the accumulation of antimicrobial agents and formation of physical barriers such as, lignification, suberization, formation of callose and papillae, accumulation of agglutinins, enzyme inhibitors and hydroxyproline-rich glycoproteins.

Another mechanism for ISR in plants is believed to be the production of hydrolytic enzymes (such as chitinases and β-1,3-glucanases), other pathogenesis related (PR-) proteins, and anionic isozymes of peroxidases. It has been reported that at least 12 such proteins accumulate in symptomatic tissue extracts in cabbage following challenge with pathogenic *Xanthomonas campestris* pv. *campestris*, the causative organism of black rot.

Plant chitinases are reported to be potent inhibitors of fungal growth and in combination with β-1,3-glucanase attack a number of fungi. Chitinases also possess lysozyme activity for hydrolyzing peptidoglycans present in bacterial cell walls. Chitinase and β-1,3-glucanase are coordinately induced in a number of plant tissues by pathogen attack and elicitors.

Peroxidases, which generate $H_2O_2$ and oxidize phenols, are important in lignin biosynthesis. Enhanced peroxidase activity has been found in immunized cucumber, muskmelon, tobacco and watermelon plants.

ISR can be transmitted by asexual means of propagation such as tissue culture and grafts. ISR is systemic, whereas with non-systemic chemicals applied to plants, areas of the plant not covered with the chemical may not be resistant to infection.

Unfortunately, because many pathogenic organisms require a wound in order to guarantee inoculation of the plant, current methods of inducing ISR in plants have proven unsatisfactory. Inoculation today is achieved by the labor intensive method of individually injecting or wounding a plant so that non-pathogenic organisms can enter to induce ISR. This method has proven to be impractical and not always as effective as required for modern large scale agriculture.

A list of publications relating to the Background of the Invention or of interest is provided herein below under "references".

It is evident from this background review that inducing immunity in plants presents a serious problem and that, though numerous methods have been proposed, no satisfactory solution has yet been found. This invention contributes to the solution of this world-wide problem by inducing natural defense mechanisms with a novel, safe, reliable and convenient formulation which is applied to the target plants.

VARIOUS EMBODIMENTS OF THE INVENTION

Figure 1A:
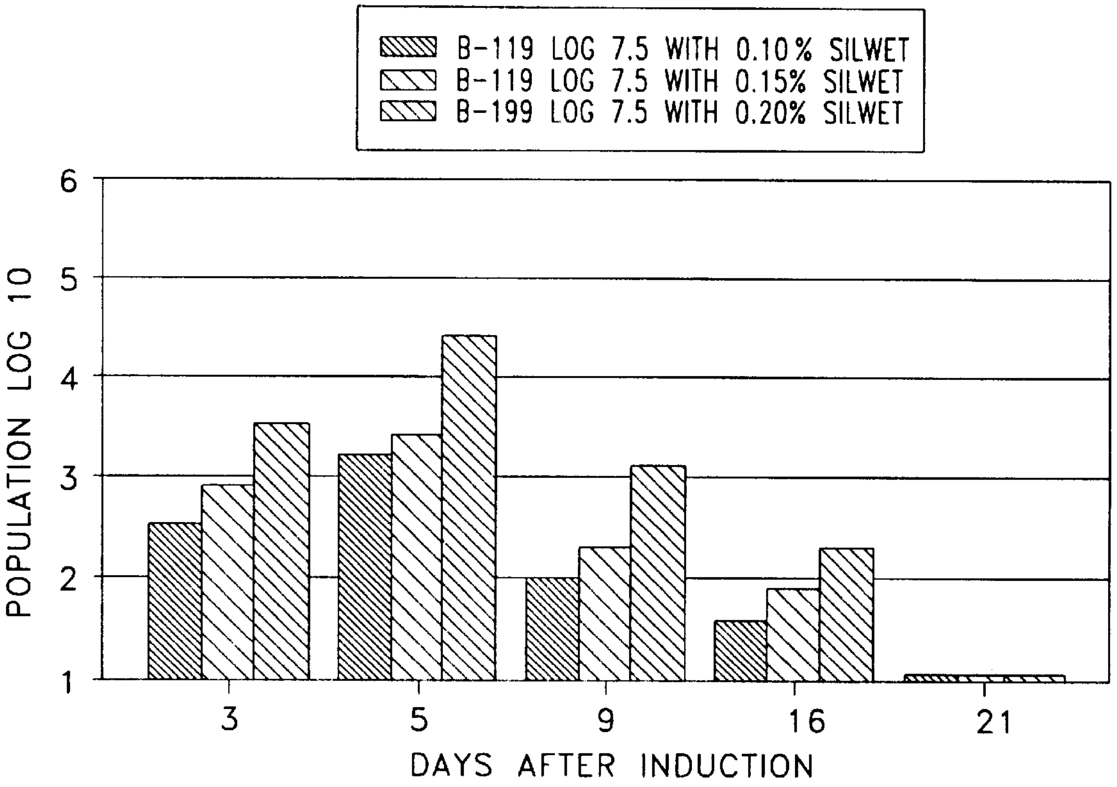
FIGS. 1A and 1B show the effect of surfactant rates on mean populations of WXcc and of Xcm in planta.

The invention has several embodiments. An important embodiment of the invention provides a formulation which upon application to the surface of a plant, like its leafy parts, immunizes the target plant against pathogens of the target plant. The formulation of the invention comprises a chemical molecule which provides penetration of a selected immunizing (inducer) microorganism into the plant. The immunizing microorganism is not pathogenic to the target plant or is only weakly so.

In a preferred aspect of the invention, the molecule is a surfactant which reduces the surface tension of the treated plant part to a value at which liquids such as water have approximately a zero contact angle on the treated surface of the target plant.

In a preferred aspect of the invention, the immunizing inducer microorganism is naturally a non-pathogen to the target plant.

Other embodiments of the invention include a method for applying the composition to a target plant.

In a further embodiment, the invention provides plants, especially crops, which have induced immunity against pathogenic microorganisms to the target plant. In a particularly useful aspect, the immunity is long lasting, often until harvest time. If desired, a booster immunization can be applied at a later date after initial application of the formulation. The booster immunization may be applied if the initial immunity appears to be fading, that is, if the plants develop symptoms which approach the economic threshold (see Example 4).

It is another noteworthy aspect of the invention that the immunizing microorganism propagates for only a short time (up to from 5 to 12 days) in the target plant and later dies after a period of decline. It could have been expected, particularly with non-pathogenic endophytic (usually symbiotic) organisms and attenuated pathogens to target plants, that the microorganism would continue to develop in the plant tissues. With respect to microorganisms which are pathogenic to plants other than the target plant, it could have been expected that the microorganism would not even develop in the target plant.

Other embodiments of the invention will become apparent from the teachings of the description of the invention.

It was not expected that a non-ionic wetting agent could induce immunity of a plant without adverse disruption of the tissues of the plant so that no or little detrimental effects would result. Further, it was not foreseen that a pathogen which normally is not identified as a pathogen to the target plant, would induce immunity to the target plant when used in accordance with the invention with a non-ionic wetting agent.

It was a surprising observation that, in accordance with the invention, proteins were expressed after immunization so rapidly and in a spectrum (and in different proportions relative to each other) different from what had been observed heretofore. Specifically, it was observed that defense proteins, including chitinase/lysozyme, β-1,3-glucanase and osmotin accumulated rapidly. In untreated controls, these proteins only accumulated after disease development.

There appears to be no published general principle that would teach that non-pathogens to a plant could provide easily applicable immunity to the plant as discovered in accordance with the invention.

SUMMARY OF THE INVENTION

The invention relates to a method for immunizing or inducing systemic resistance (ISR) in plants against a broad range of pathogens. The method of the invention comprises the application of a formulation containing an inducer which may be a microorganism which is non-pathogenic for the target plant, the non-pathogenic microorganism being a microorganism which is recognized in the relevant literature to be naturally not pathogenic to the target plant or is naturally pathogenic to the plant but which has been attenuated so that it is no longer pathogenic or is only weakly pathogenic to the target plant, and a molecule which promotes penetration of the microorganism into the plant. In accordance with the invention, it has been observed that this results in the production of defense proteins prior to the onset of symptoms of the disease in a pattern and at times different from what was known in the art. The method causes a long lasting non-specific systemic immunity of the plant (and of asexual progeny) to disease when challenged with a pathogenic organism.

As used herein, an "inducer" is a microorganism which is a weak pathogen, attenuated pathogen, a pathogen of another host plant, a non-pathogen of any plant, or a chemical product of these organisms that sensitizes a plant inoculated with the inducer to produce disease defense products that reduce disease and which do not produce overt levels of disease (above economic threshold as defined herein below) although a visible level of pathology may be observed.

The terms "non-pathogenic" and "not pathogenic" also include strains of naturally pathogenic bacteria to the target plant which are weakly pathogenic, that is, that do not cause disease at or above the level of the economic threshold, as defined herein below as v-shaped lesions 1.0 to 2.0 cm in diameter with distinct marginal chlorosis and blackened veins within the lesion at older leaves and younger leaves showing necrotic lesions starting systemic disease.

The method of the invention may be used to immunize a great variety of plants, including vegetable and fruit crops, cereals, fruit trees, berries, forestry trees, ornamental plants, and other plants such as coffee and cotton. Any plant with stomates, hydathodes nectaries or lenticels may be immunized with the method of this invention.

The inducer used in the invention may be a microorganism which is naturally pathogenic to the plant but which has been attenuated so that it is no longer pathogenic or is only weakly pathogenic to the target plant. The inducer may be a microorganism which is pathogenic for a plant other than the target plant and which is not pathogenic for the target plant. Alternatively, the inducer may be a natural non-pathogen of any plant.

It is envisioned that if the chemical generated by the immunizing organism or a component of the organism itself responsible for ISR can be isolated, that it too would be delivered through natural plant openings to induce resistance in the plant using the methods of this invention. Thus, the chemical can be delivered without the microorgansim. The inducer may be a virus, a bacterium, a fungus or their products that is involved in inducing resistance. Non-limiting examples of suitable viruses include tobacco necrosis virus (TNV) and tobacco mosaic virus (TMV), suitable fungi include *Collectotrichium lagenarium*, the causative organism of anthracnose, *Peronospora tabacina*, the causative organism of blue mold in tobacco, and *Fusarium oxysporum*, vascular wilt and damping of on many plants and suitable bacteria include *Xanthomonas campestris* and *Pseudomonas spp.*

It was surprising to observe that the pathogen of a plant other than the target plant was an equal or better inducer than the weak pathogen of the target plant, even though the pathogen of another plant produced much less visible pathology. It had previously been assumed that at least a moderate level of pathology (necrosis) was required to induce high levels of protection.

A screening test to identify suitable microorganisms for purposes of inducing ISR in a target plant species has been developed in accordance with the invention.

A suspension of the microorganism in surfactant, in a suitable buffer, is formulated as described herein below. Three groups of target plants are established, one group is not treated, a second group is treated with the formulation not containing the microorganism, and a third group is treated with the formulation containing the microorganism. The formulation is applied to young plants as described herein below.

Gel electrophoresis of the proteins of the three groups of plants is performed and the results of each group are compared as described below in Example 10 and in FIGS. 14*a–d*. If the plants treated with the formulation with microorganism produce defense proteins earlier and at higher levels compared with plants treated with the formulation without the microorganism and with untreated plants, the microorganism is suitable for use as an immunity inducing microorganism. Conversely, if the formulation plus microorganism treated plants do not produce higher levels of defense proteins compared with plants treated with the formulation without the microorganism and with untreated plants, the microorganism can be considered as not adequately suitable for use as an immunity inducer.

The molecule of the invention which promotes penetration of the microorganism into the plant is preferably a surfactant. The surfactant is preferably a nonionic surfactant. A non-ionic surfactant that belongs to the class of polysilicone trisiloxane surfactants has been found to be quite suitable. In accordance with the invention, it has been observed that a surfactant which lowers the surface tension to a level below the degree at which the critical angle of water is zero, thus causing flooding of stomata and/or hydathodes, may be used.

The surfactant used in the formulation of the invention may be polyalkyleneoxide modified polydimethylsiloxane copolymer (Silwet L-77™, Union Carbide, Tarrytown, N.Y.), having the formula

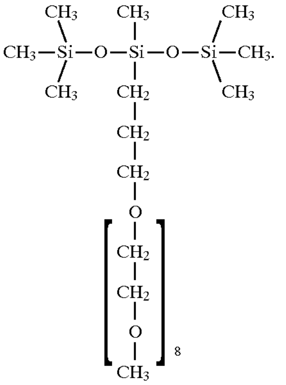

Other suitable surfactants include 2-(3-hydroxypropyl) heptamethyltrisiloxane ethoxylated acetate (Sylgard-309™, Wilbur Ellis, San Francisco, Calif.) and proprietary blends of polyalkyleneoxide modified polydimethylsiloxane and non-ionic organosilicone adjuvants. These are available commercially under the following trade names Kinetic™, Helena Chemical Co., Memphis Tenn. and Silenergy™, Brewer International Inc., Vero Beach, Fla.

The invention also includes a formulation for conferring ISR in plants comprising either an attenuated pathogenic organism for the target plant or a naturally non-pathogenic organism for the target plant, which may be an endophyte. Mixtures of both may be used. Methods of attenuation of microorganisms are well known in the art, including transposon, ultraviolet and chemical mutagenesis.

The formulation may include appropriate buffers, which may be a phosphate buffer. The pH is generally in the neutral range from about 5–8. The molarity is usually around 0.1M.

Other compounds may be incorporated into the formulation, providing they do not detract from the effect of the essential components of the invention. With higher rates of microorganisms in the formulation, the resistance of the immunized plant is higher in terms of reduced disease severity and growth of pathogenic organisms. If bacteria are used as the immunizing microorganism, the concentration of microorganisms may be log 9.0 colony forming units/ml of formulation. Lesser concentrations of microorganisms, between log 7.0 and log 9.0 cfu/ml, may be used if lower levels of immunity are acceptable.

With increasing concentrations of surfactant, higher levels of the microorganisms are able to penetrate the plant, thus conferring a greater degree of resistance. At high levels of surfactant concentration, the benefit of the increased immunity conferred to the plant may be offset by the damaging effects of the surfactant. In the case of polyalkyleneoxide modified polydimethylsiloxane copolymer, concentrations of 0.25% v/v or higher tend to cause undesirable effects in cabbage. Other plants, however, may be more or less tolerant so that the upper limits can be readily determined for each group of target plants. Thus, in a preferred embodiment, the concentration of surfactant is about 0.2%, v/v, a level of surfactant which has not been observed to cause significant deleterious effects in treated plants. Levels of surfactant as low as about 0.1% v/v may be used if a lesser degree of immunity is acceptable, and/or less damage to the plant is desirable.

The invention also includes a method of application of the formulation by contacting the formulation to the surface of a plant to cause penetration of the active component of the formulation and of a microorganism into the stomata and/or hydathodes. Application may be by spraying the leaves of the plant until the leaves are partially wetted, wetted, or until runoff. The formulation may be applied at any time of day or night with good immunization resulting, but preferentially while stomates are open which occurs during day light.

Although the method of the invention provides for the surfactant and the microorganism to be applied concurrently to the target plant. It is conceivable that these components can be applied sequentially (in any desired sequence) so long as each component will perform as intended in accordance with the invention.

The application of the formulation can be repeated as often as considered desirable, with one or more "booster" applications applied to bolster immunity should the previously induced immunity begin to fade, as evidenced by the onset of disease symptoms. Thus, the formulation may be considered "prophylactic" as well as "therapeutic". The booster application results in renewed increased production of defense proteins.

It has been observed that plants immunized in accordance with the invention produce a multicomponent defense system which includes defense proteins, such as chitinase/lysozyme2 (CHL2), β-1,3-glucanase, peroxidases, and osmotin, and as envisioned, low molecular weight antimicrobial compounds called phytoalexins. It has also been found that these defense products are produced more rapidly and/or at a higher level in immunized plants than in plants that are not treated or plants that are treated with a formulation not containing immunizing microorganisms.

In contrast to non-treated plants, immunized plants produce the defense products before challenge with a pathogen. Additionally, immunized plants produce defense products in response to challenge with a pathogen more rapidly and at significantly higher levels than do non-immunized plants. Both higher total levels of defense proteins are produced and higher levels of each defense protein are produced by immunized plants than by non-immunized plants.

It has also been noted that different defense proteins are produced in immunized plants than in non-immunized plants and the relative proportions of generated proteins is different from those generated not in accordance with the invention.

It has been observed that the production of the defense products in accordance with the invention results in a systemic immunity that lasts at least several weeks (for instance, 4 to 6 weeks) and may last throughout the growing season and/or throughout the life of the plant. Alternatively, treatment with the method of the invention may result in something less than total immunity to disease. Such reduced immunity may be resistance to diseases. Such resistance may not be a total immunity but will reduce the growth of pathogenic organisms adequately and will reduce pathologic effects of those organisms. As described herein, the terms "immunity" and "resistance" are used interchangeably and refer to increased resistance to the growth and pathogenic effects of pathogenic organisms, which resistance may be total or somewhat less than total. "Induced Systemic Resistance" ("ISR") is also used interchangeably with the terms "immunity" and "resistance".

An important advantage of the invention is that, unlike chemical means of disease control in plants, the formulation and method of the invention are environmentally friendly and safe.

It is an unexpected advantage of the invention that the immunity induced by the method of the invention is non-specific. Plants treated in accordance with the method of the invention have been found to be resistant to pathogen growth and disease from a broad range of pathogens, including bacteria, fungi, and viruses. This non-specificity is in contrast to the immunity of resistant cultivars and to chemical methods of disease control. Because of this non-specificity, ISR induced by means of the invention can protect plants from pathogens against which no antimicrobial agents are yet known.

Additionally, unlike disease control with chemical means, the immunity resulting from treatment according to the method of the invention has been found to be transmissible to progeny of plants propagated by asexual means such as grafting and through tissue culture. Thus, the present invention also includes the plants immunized by the application of the formulation of the invention and the progeny of the plants propagated by asexual means such as tissue culture or grafting.

An unexpected aspect of the invention is that the immunizing microorganism has been found to be short lived as opposed to developing within the target plant. The immunizing organism survives for two to three weeks in the target plant, as compared to pathogenic bacteria which survive for longer periods and cause disease to the host plant. The immunizing organisms appear to be killed by the ISR defense products. Thus, it has been found in accordance with the invention that the period of ISR induced by the formulation of the invention is not concurrent with the period of the live immunizing microorganism but persists even after the inducing microorganism is no longer alive in the target plant.

Though the invention is illustrated by specific microorganisms as described herein, by non-ionic surface active molecules, and by certain typical target plants, the fundamental principle of the invention suggests that the formulation -and the method- have broad applicability which allow selection of different active components for the formulation and the plants to which immunization is imparted.

DETAILED DESCRIPTION OF THE DRAWINGS

Figure 1B:
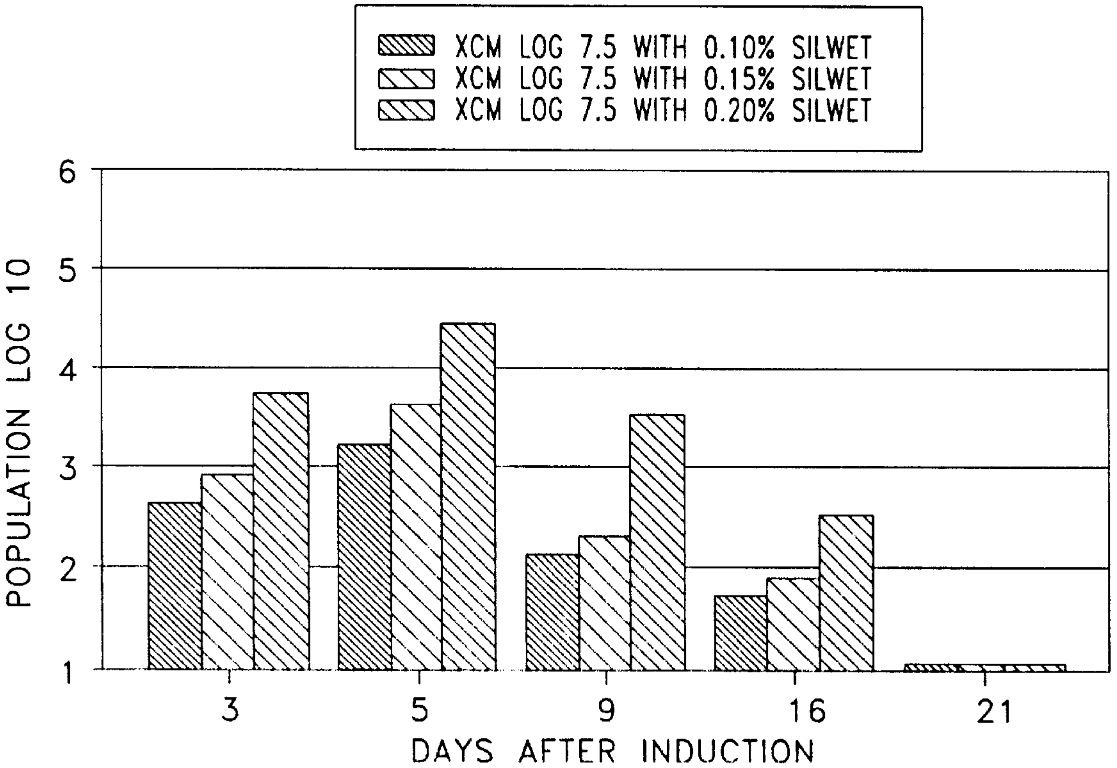

FIG. 1 shows the effect of surfactant rates on mean populations of (A) the *Xanthomonas campestris* pv. *campestris* isolate B-119 in planta. (B) the incompatible pathogen *X. c.* pv. *malvacearum* in planta.

Figure 2A:
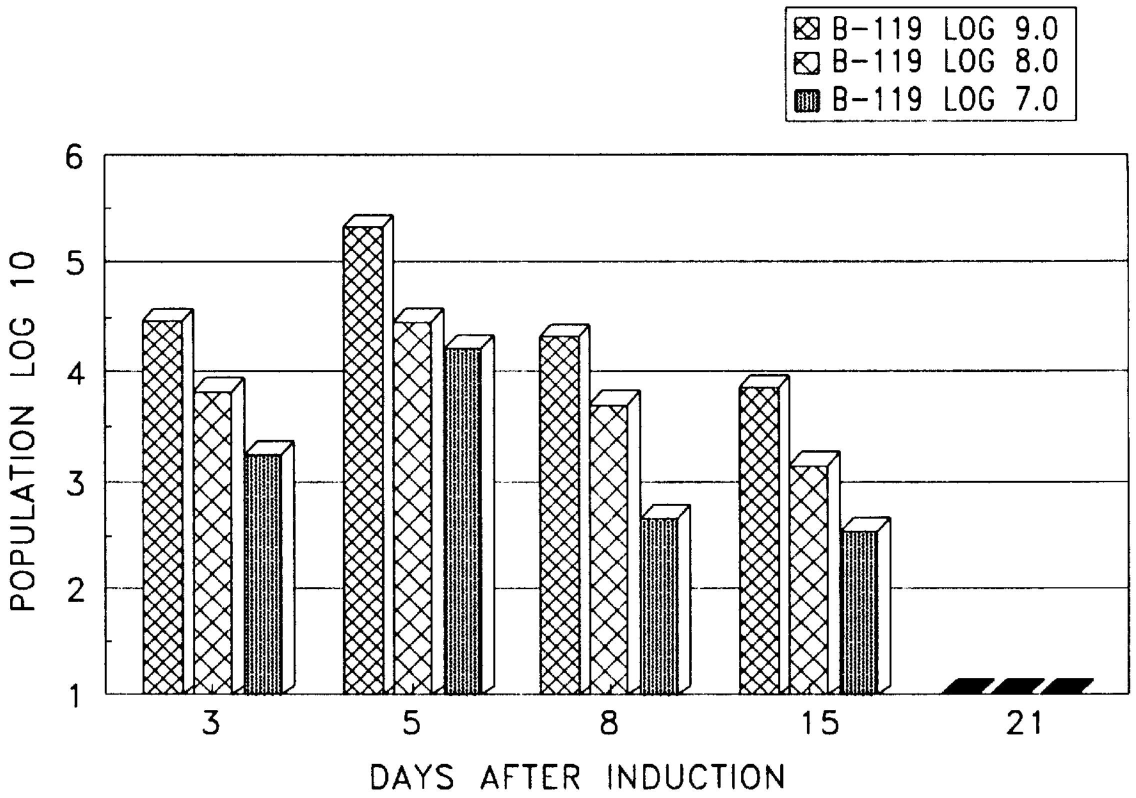
FIGS. 2A and 2B show the mean populations of three rates of WXcc and of Xcm in cabbage leaves 3, 5, 9, 15, and 21 days after induction.
Figure 2B:
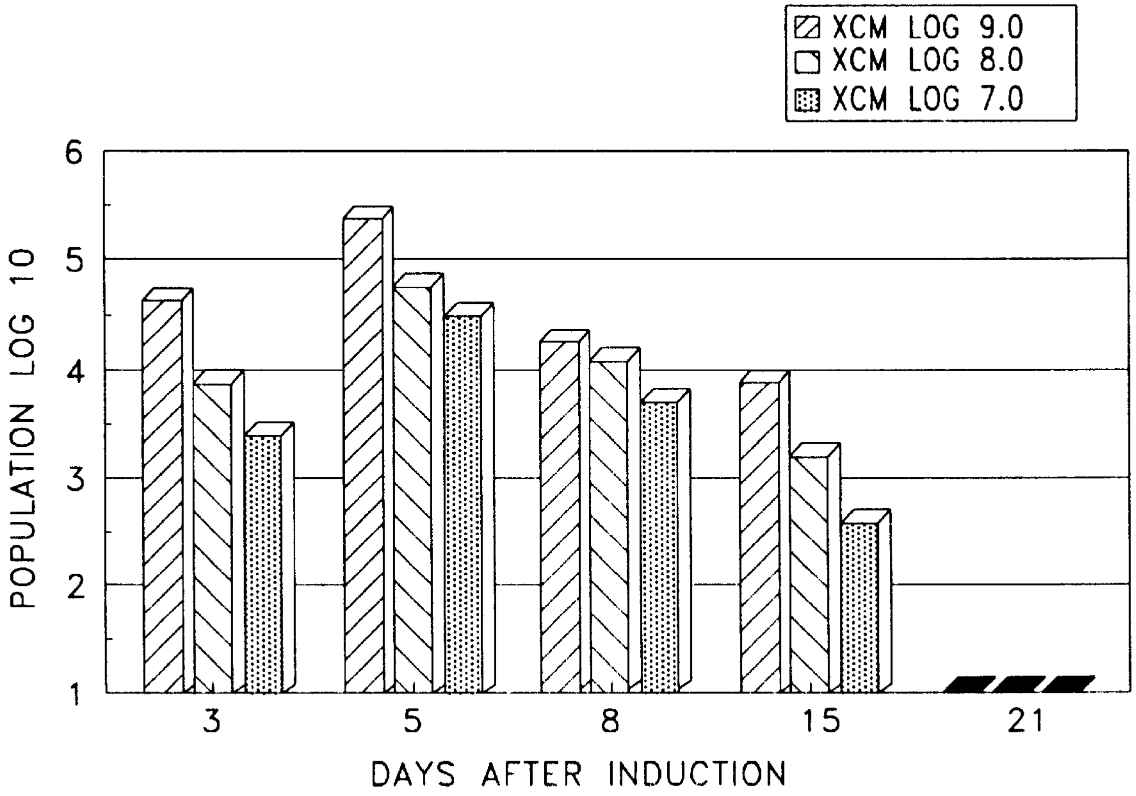

FIG. 2A shows the mean populations of three rates of the *Xanthomonas campestris* pv. *campestris* isolate B-119 in cabbage leaves 3, 5, 9, 15, and 21 days after induction. FIG. 2B shows the mean populations of three rates of the incompatible pathogen *X.c.* pv. *malvacearum* in cabbage leaves also at 3, 5, 9, 15, and 21 days after induction.

Figure 3:
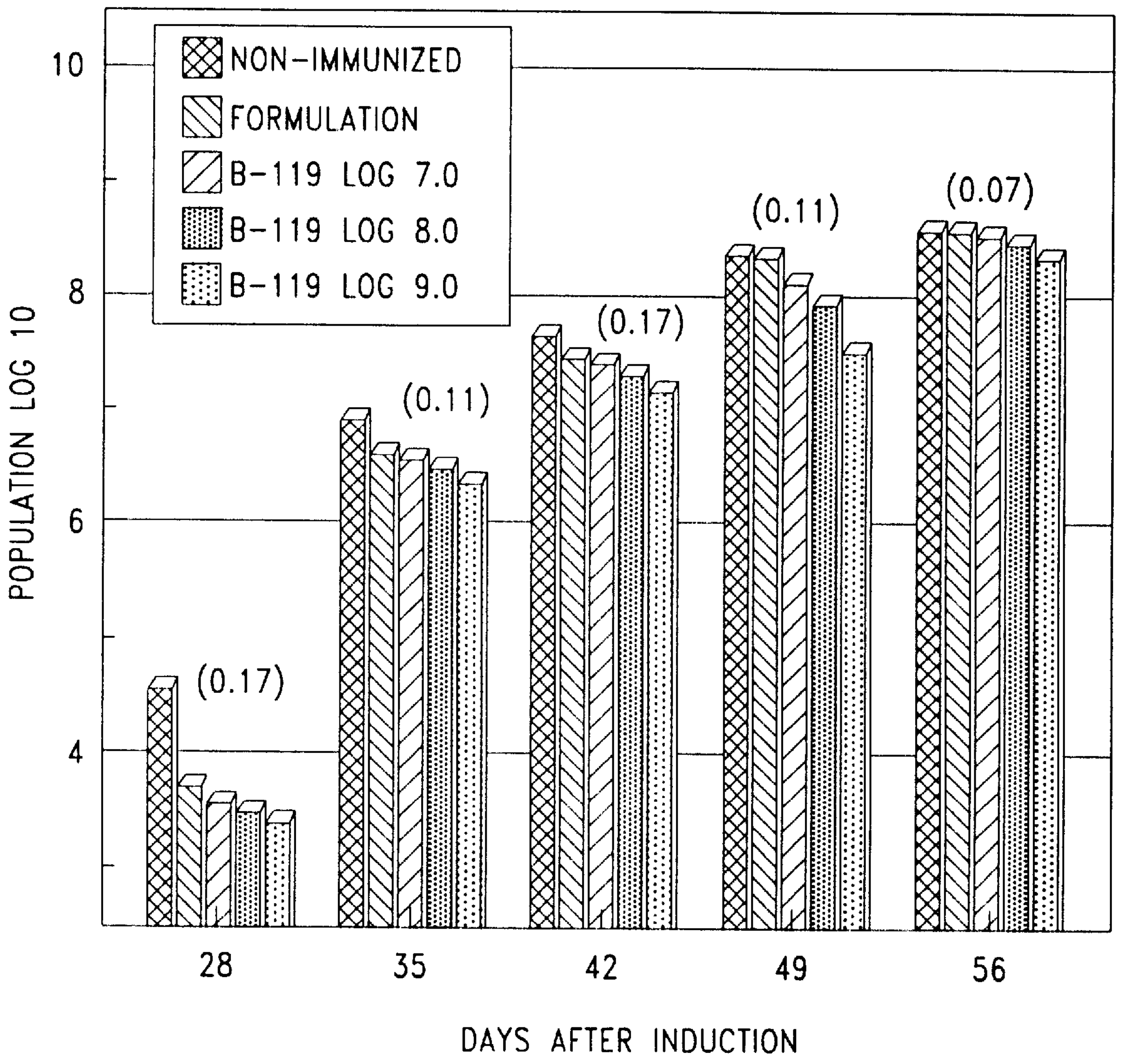
FIG. 3 shows the mean populations of pathogenic Xcc after challenge in cabbage leaves treated 21 days earlier with either the formulation control (0.2% surfactant plus 0.1M phosphate buffer), formulation plus three rates (log 9.0, log 8.0, and log 7.0 cfu/ml) of WXcc, and non-immunized plants.

FIG. 3 shows the mean populations of the pathogenic *Xanthomonas campestris* pv. *campestris* (Xcc) after challenge in cabbage leaves treated 21 days earlier with either the formulation control (0.2% surfactant plus 0.1M phosphate buffer), formulation plus three rates (log 9.0, log 8.0, and log 7.0 cfu/ml) of the weakly pathogenic Xcc isolate B-119, or non-treated plants. Cabbages were induced at day 0 and challenged at day 21. Numbers in () represent LSD (P=0.01).

Figure 4:
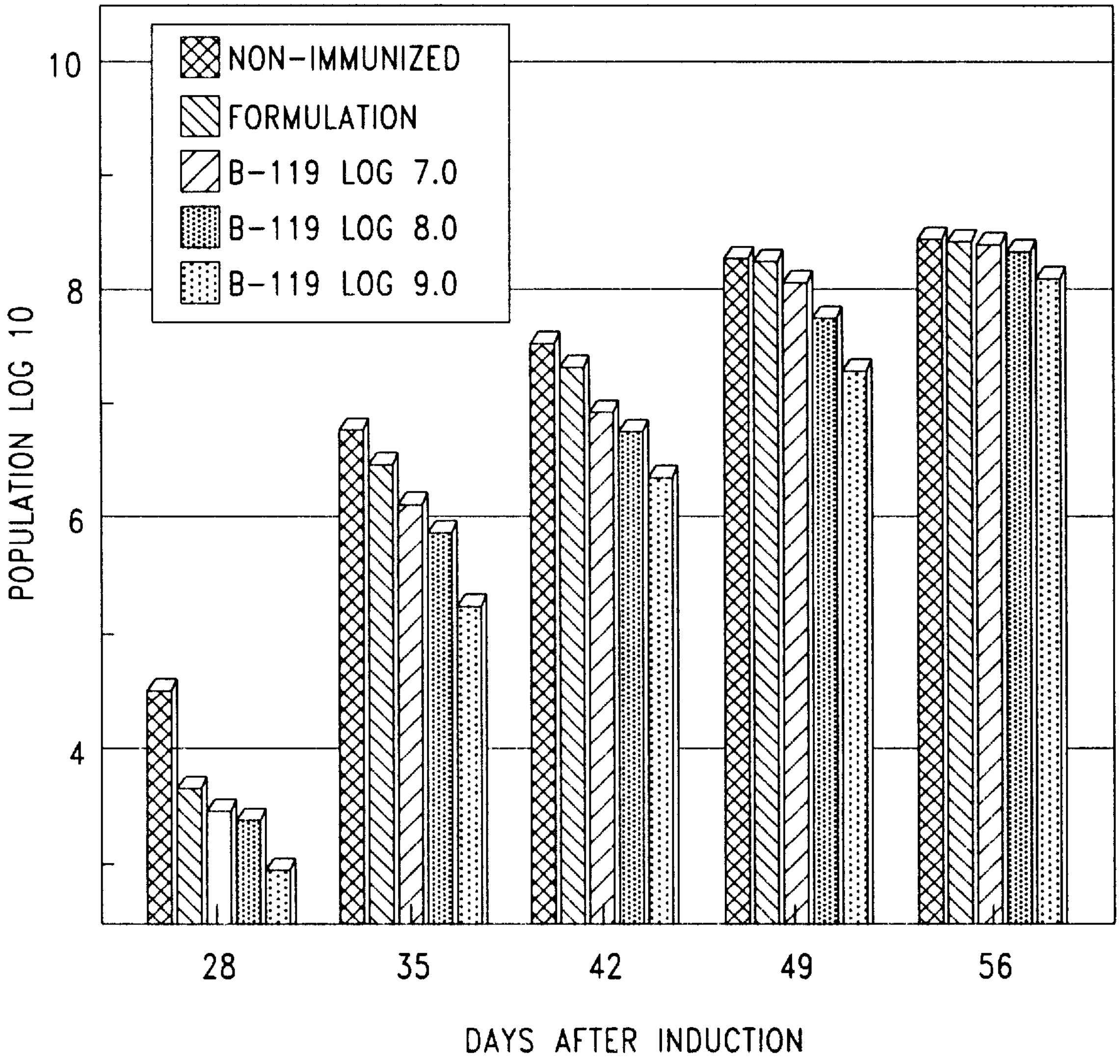
FIG. 4 shows the mean populations of the pathogenic *Xanthomonas campestris* pv. *campestris* after challenge in cabbage leaves treated 21 days earlier with either the formulation control (0.2% surfactant plus 0.1M phosphate buffer), formulation plus three rates (log 9.0, log 8.0, and log 7.0 cfu/ml) of Xcm, or nonimmunized plants.

FIG. 4 shows the mean populations of the pathogenic *Xanthomonas campestris* pv. *campestris* after challenge in cabbage leaves treated 21 days earlier with either the formulation control (0.2% surfactant plus 0.1M phosphate buffer), formulation plus three rates (log 9.0, log 8.0, and log 7.0 cfu/ml) of an incompatible pathogen *X. c.* pv. *malvacearum*, or nontreated plants. Cabbages were induced at day 0 and challenged at day 21. Numbers in () represent LSD (P=0.01).

Figure 5:
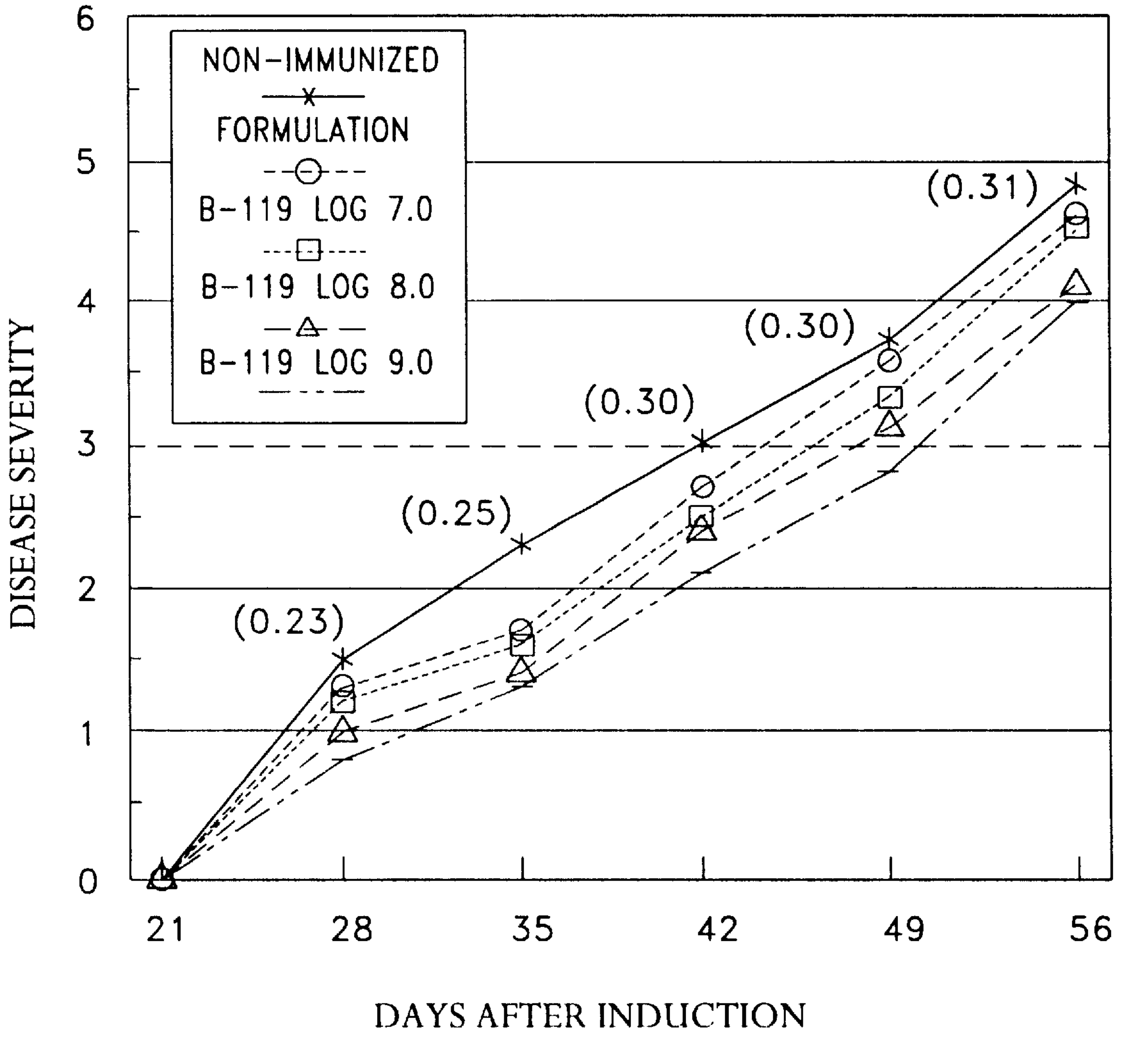
FIG. 5 shows the mean disease severity of black rot after challenge with pathogenic Xcc on greenhouse grown cabbages treated 21 days earlier with the formulation control (0.2% surfactant plus 0.1M phosphate buffer), formulation plus three rates (log 9.0, log 8.0, and log 7.0 cfu/ml) of WXcc, or non-immunized plants.

FIG. 5 shows the mean disease severity of black rot after challenge with the pathogenic *Xanthomonas campestris* (Xcc) on greenhouse grown cabbages treated 21 days earlier with the formulation control (0.2% surfactant plus 0.1M phosphate buffer), formulation plus three rates (log 9.0, log 8.0, and log 7.0 cfu/ml) of the weak pathogenic Xcc isolate B-119, or non-treated plants. The bold line at level 3.0 represents the economic threshold. Cabbages were induced at day 0 and challenged at day 21. Numbers in () represent LSD (P=0.01).

Figure 6:
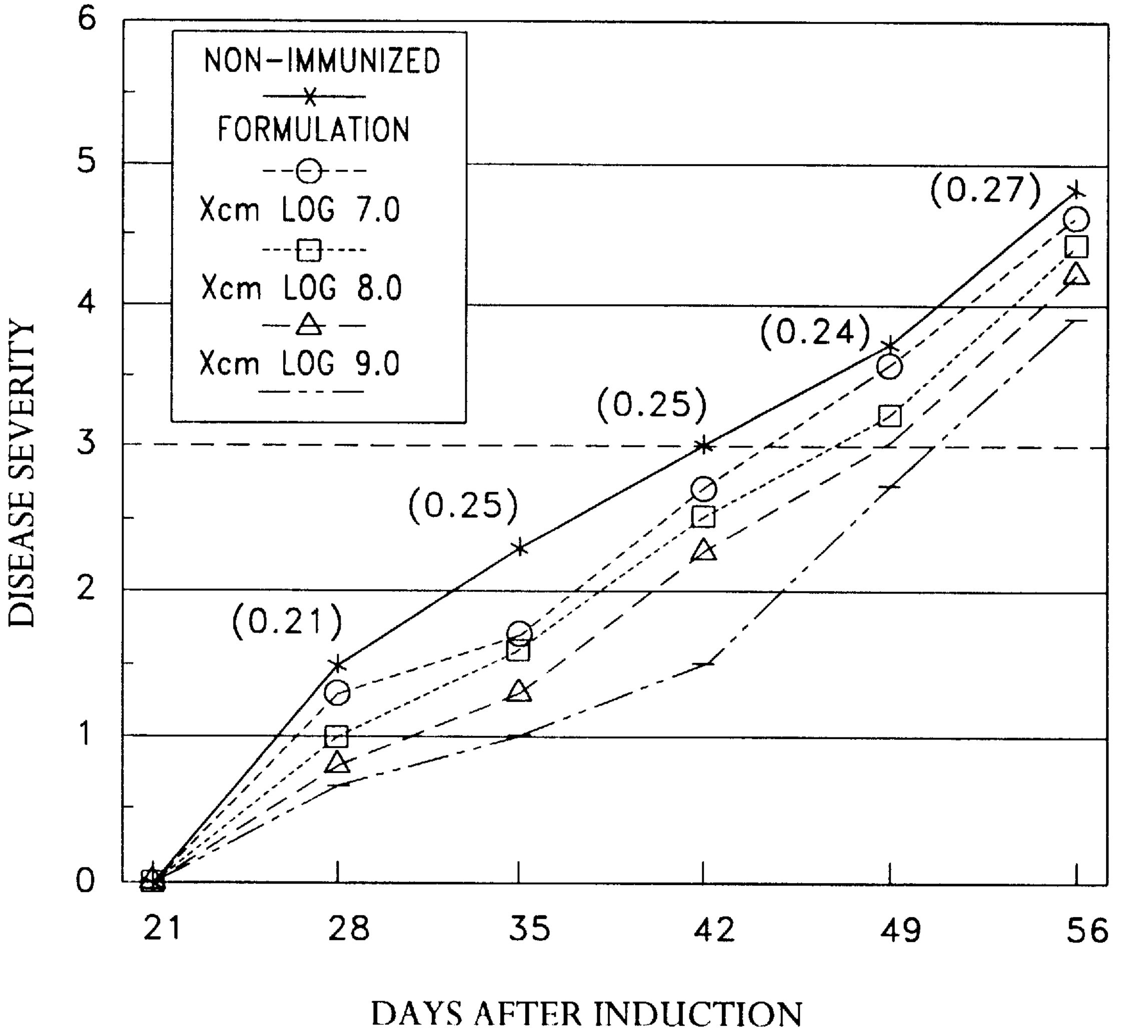
FIG. 6 shows the mean disease severity of black rot after challenge with pathogenic Xcc on greenhouse grown cabbages treated 21 days earlier with either the formulation (0.2% surfactant plus 0.1M phosphate buffer), formulation plus three rates (log 9.0, log 8.0, and log 7.0 cfu/ml) of Xcm, or non-immunized plants.

FIG. 6 shows the mean disease severity of black rot after challenge with the pathogenic *Xanthomonas campestris* pv. *campestris* (Xcc) on greenhouse grown cabbages treated 21 days earlier with either the formulation (0.2% surfactant plus 0.1M phosphate buffer), formulation plus three rates (log 9.0, log 8.0, and log 7.0 cfu/ml) of the incompatible pathogen *X. c.* pv. *malvacearum* alone, or non-treated plants. The bold line at level 3.0 represents the economic threshold. Cabbages were induced at day 0 and challenged at day 21. Numbers in () represent LSD (P=0.01).

Figure 7:
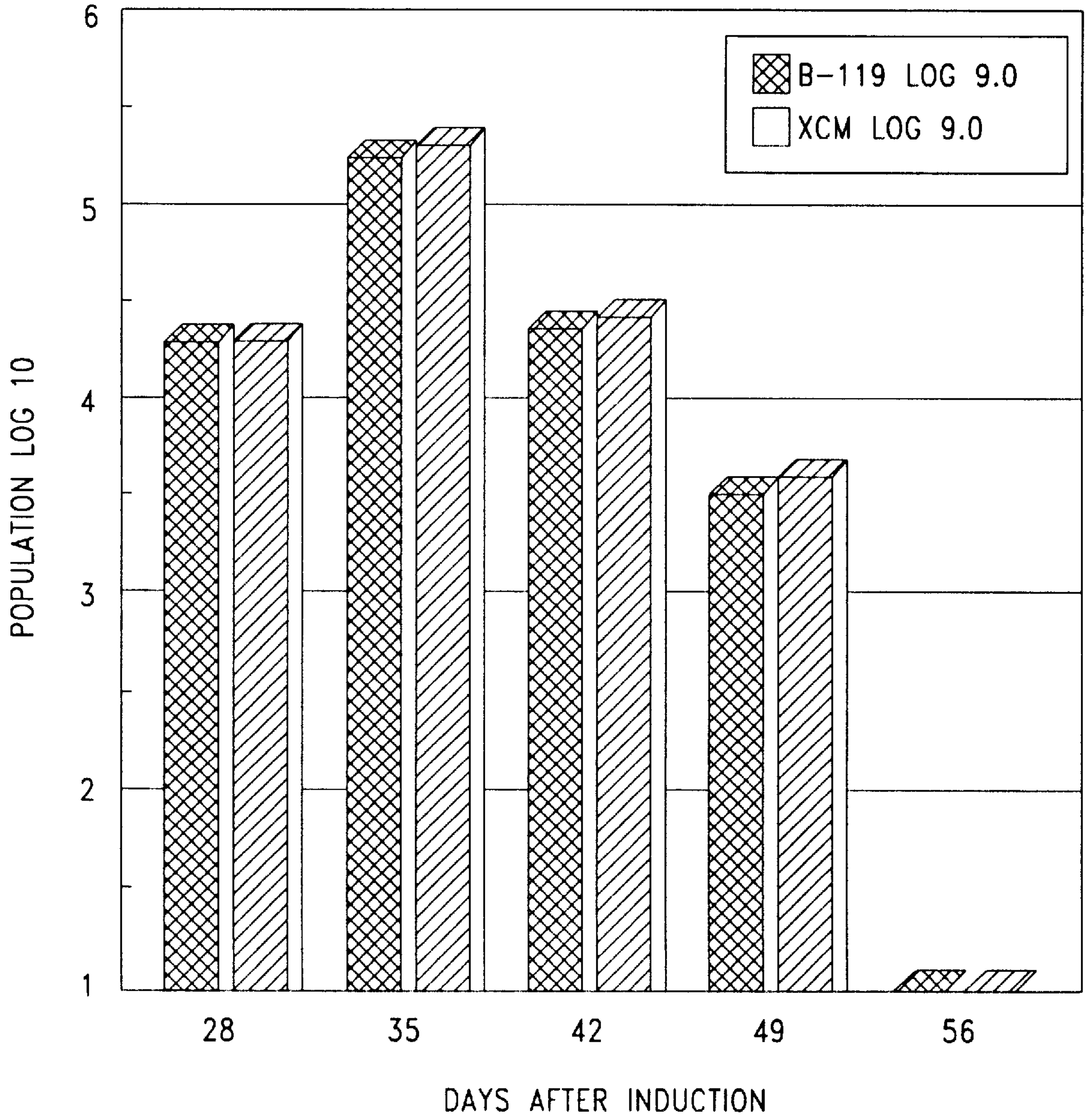
FIG. 7 shows the mean populations of the WXcc and Xcm in cabbage leaf samples at 3, 5, 9, 15, and 21 days after induction in the Spring 1993 field trial.

FIG. 7 shows the mean populations of the *Xanthomonas campestris* pv. *campestris* isolate B-119 and the incompatible pathogen *X. c.* pv. *malvacearum* in cabbage leaf samples at 3, 5, 9, 15, and 21 days after induction in the Spring 1993 field trial. Cabbages were induced at day 0.

Figure 8:
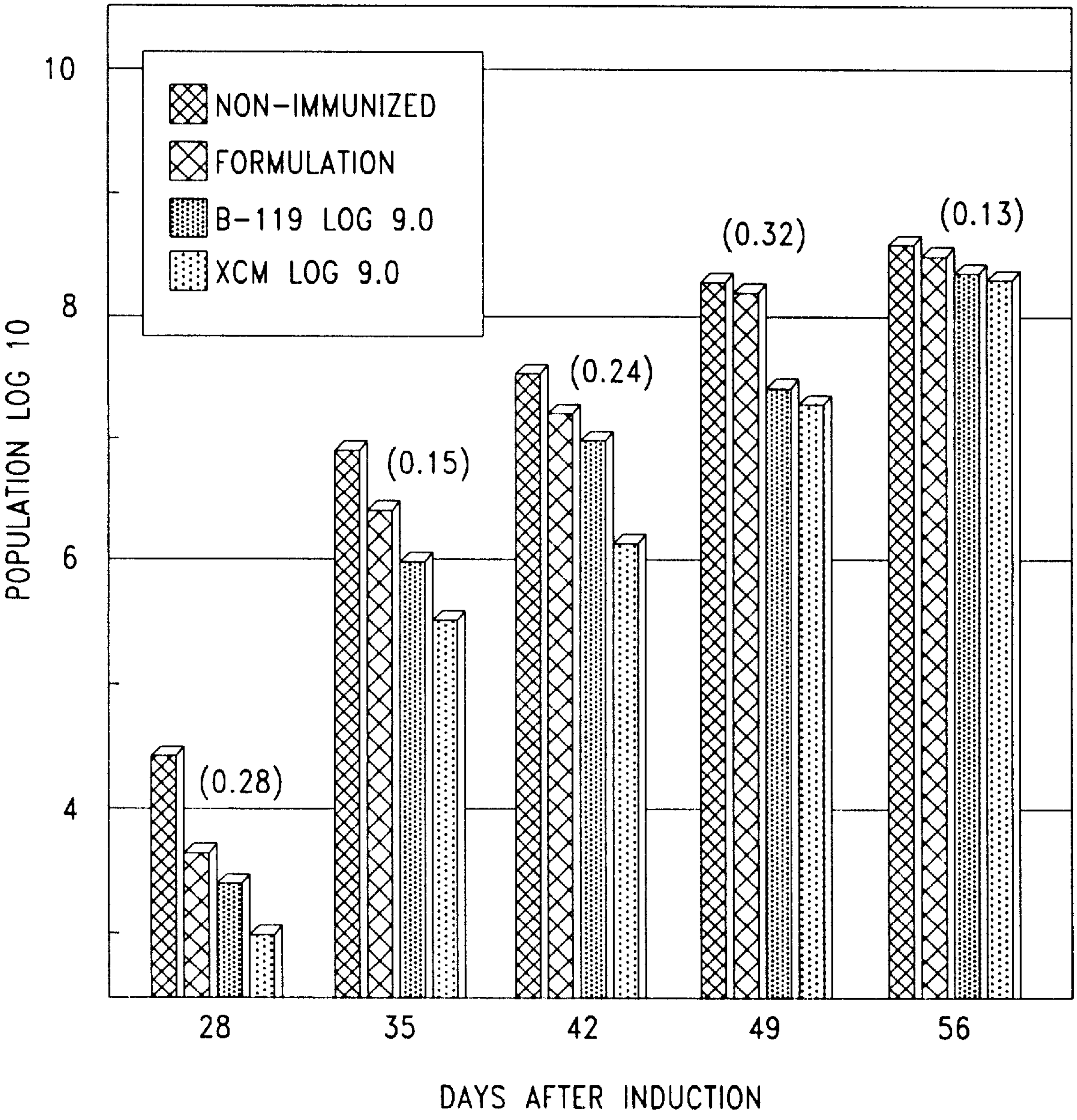
FIG. 8 shows the mean populations of the pathogenic Xcc after challenge in cabbage leaves induced 21 days earlier with either formulation control (0.2% surfactant plus 0.1M phosphate buffer), formulation plus the WXcc, formulation plus Xcm, or nonimmunized cabbages in the Spring 1993 field trial.

FIG. 8 shows the mean populations of the pathogenic *Xanthomonas campestris* pv. *campestris* (Xcc) after challenge in cabbage leaves induced 21 days earlier with either formulation control (0.2% surfactant plus 0.1M phosphate buffer), formulation plus log 9.0 cfu/ml of the weakly virulent Xcc isolate B-119, formulation plus log 9.0 cfu/ml of the incompatible pathogen *X. c.* pv. *malvacearum*, or nontreated cabbages in the Spring 1993 field trial. Cabbages were induced at day 0 and challenged at day 21. Numbers in () represent LSD (P=0.01).

Figure 9A:
FIG. 9*a* shows nonimmunized cabbage plants showing systemic black rot disease in the spring 1993 experiment at 49 days after induction.

FIG. 9A shows nonimmunized cabbage plants showing systemic black rot disease in the spring 1993 experiment at 49 days after induction. Disease rating is approximately 4.2.

Figure 9B:
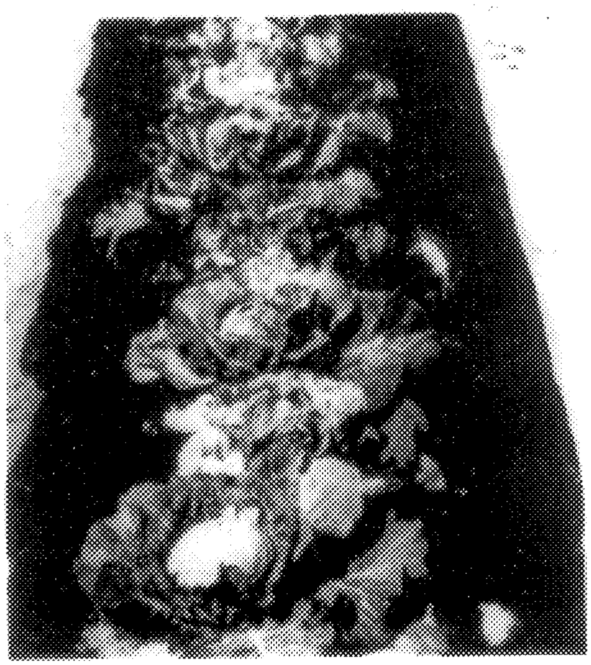
FIG. 9*b* shows immunized cabbage plants sprayed only with 0.2% surfactant plus 0.1M phosphate buffer (v/v) showing systemic black rot disease in the Spring 1993 experiment at 49 days after induction.

FIG. 9B shows cabbage plants sprayed only with 0.2% surfactant (v/v) plus 0.1M phosphate buffer showing systemic black rot disease in the Spring 1993 experiment at 49 days after induction. Disease rating is approximately 3.8.

Figure 9C:
FIG. 9*c* shows immunized cabbage plants induced with WXcc showing limited black rot disease in the Spring 1993 experiment at 49 days after induction.

FIG. 9C shows immunized cabbage plants induced with log 9.0 cfu/ml of the *Xanthomonas campestris* pv. *campestris* isolate B-119 showing limited black rot disease in the Spring 1993 experiment at 49 days after induction. Disease rating is approximately 2.8.

Figure 9D:
FIG. 9*d* shows immunized cabbage plants induced with Xcm showing limited black rot disease in the Spring 1993 experiment at 49 days after induction.

FIG. 9D shows immunized cabbage plants induced with log 9.0 cfu/ml of the incompatible pathogen *Xanthomonas campestris* pv. *malvacearum* showing limited black rot disease in the Spring 1993 experiment at 49 days after induction. Disease rating is approximately 2.8.

Figure 10:
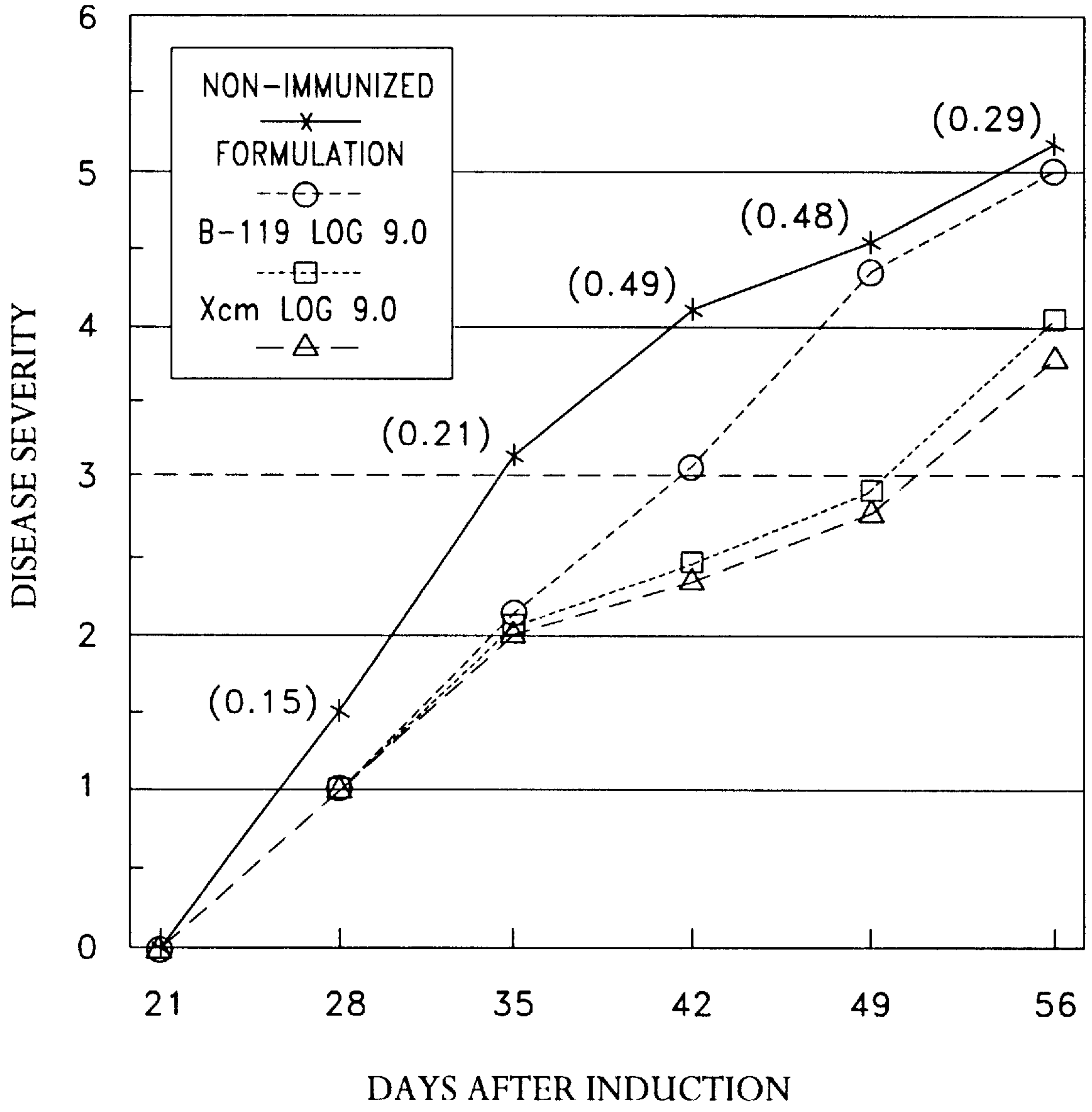
FIG. 10 shows the mean disease severity of black rot after challenge with the pathogenic *Xanthomonas campestris* pv. *campestris* (Xcc) on cabbages induced 21 days earlier with either the formulation control (0.2% surfactant plus 0.1M phosphate buffer), formulation plus WXcc, formulation plus Xcm, or nonimmunized cabbages in the Spring 1993 field trial.

FIG. 10 shows the mean disease severity of black rot after challenge with the pathogenic *Xanthomonas campestris* pv. *campestris* (Xcc) on cabbages induced 21 days earlier with either the formulation control (0.2% surfactant plus 0.1M phosphate buffer), formulation plus log 9.0 cfu/ml of the weakly virulent Xcc isolate B-119, formulation plus log 9.0 cfu/ml of the incompatible pathogen *X. c.* pv. *malvacearum*, or nontreated cabbages in the Spring 1993 field trial. The bold line at level 3.0 represents the economic threshold. Cabbage plants were induced at day 0 and challenged with a virulent Xcc isolate at day 21. Numbers in () represent LSD (P=0.01).

Figure 11:
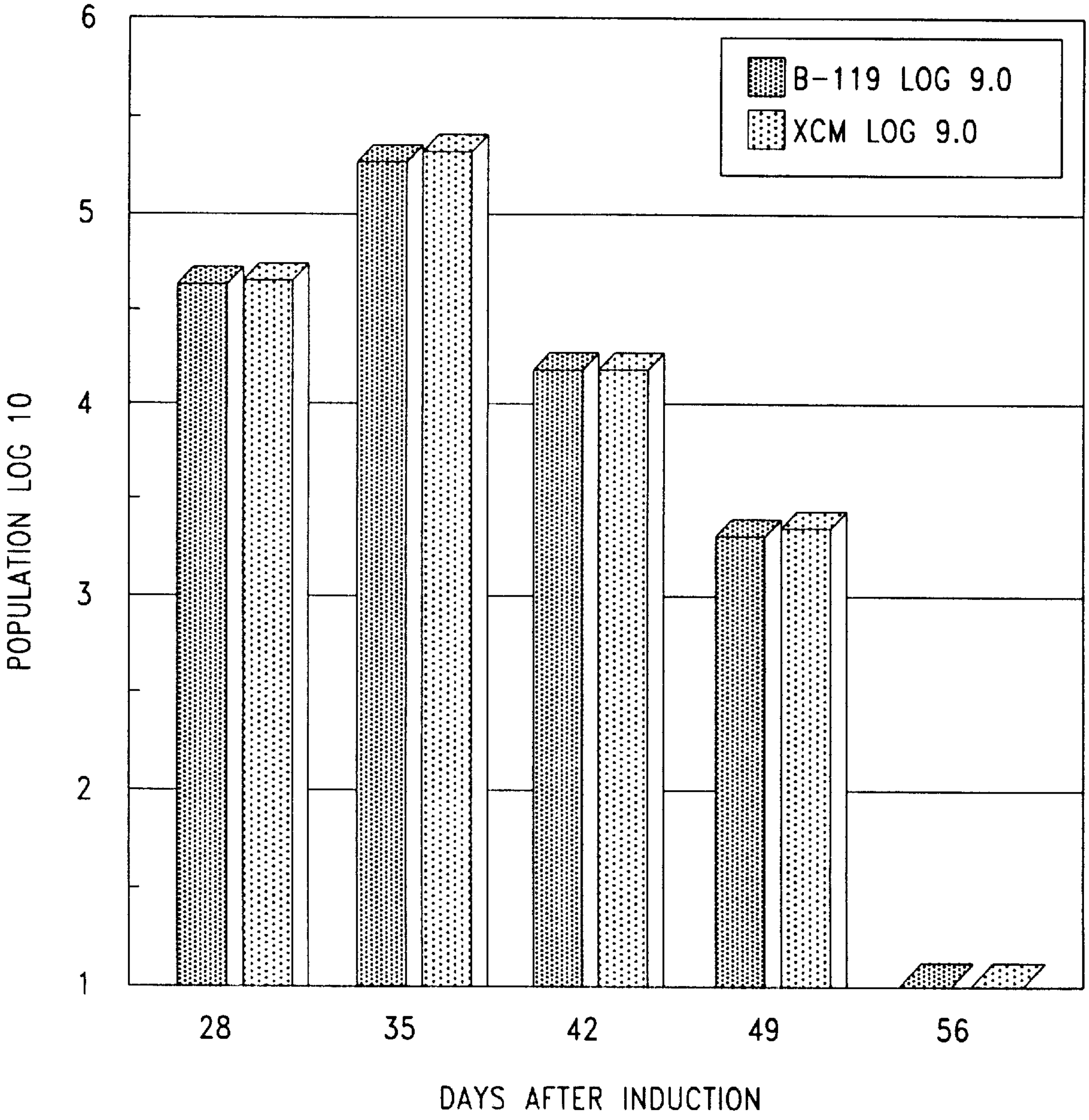
FIG. 11 shows the mean population of WXcc and Xcm in cabbage leaf samples at 3, 5, 9, 15, and 21 days after induction in the Fall 1993 field trial.

FIG. 11 shows the mean population of the *Xanthomonas campestris* pv. *campestris* isolate B-119 and the compatible pathogen *X. c.* pv. *malvacearum* in cabbage leaf samples at 3, 5, 9, 15, and 21 days after induction in the Fall 1993 field trial. Cabbages were induced at day 0.

Figure 12:
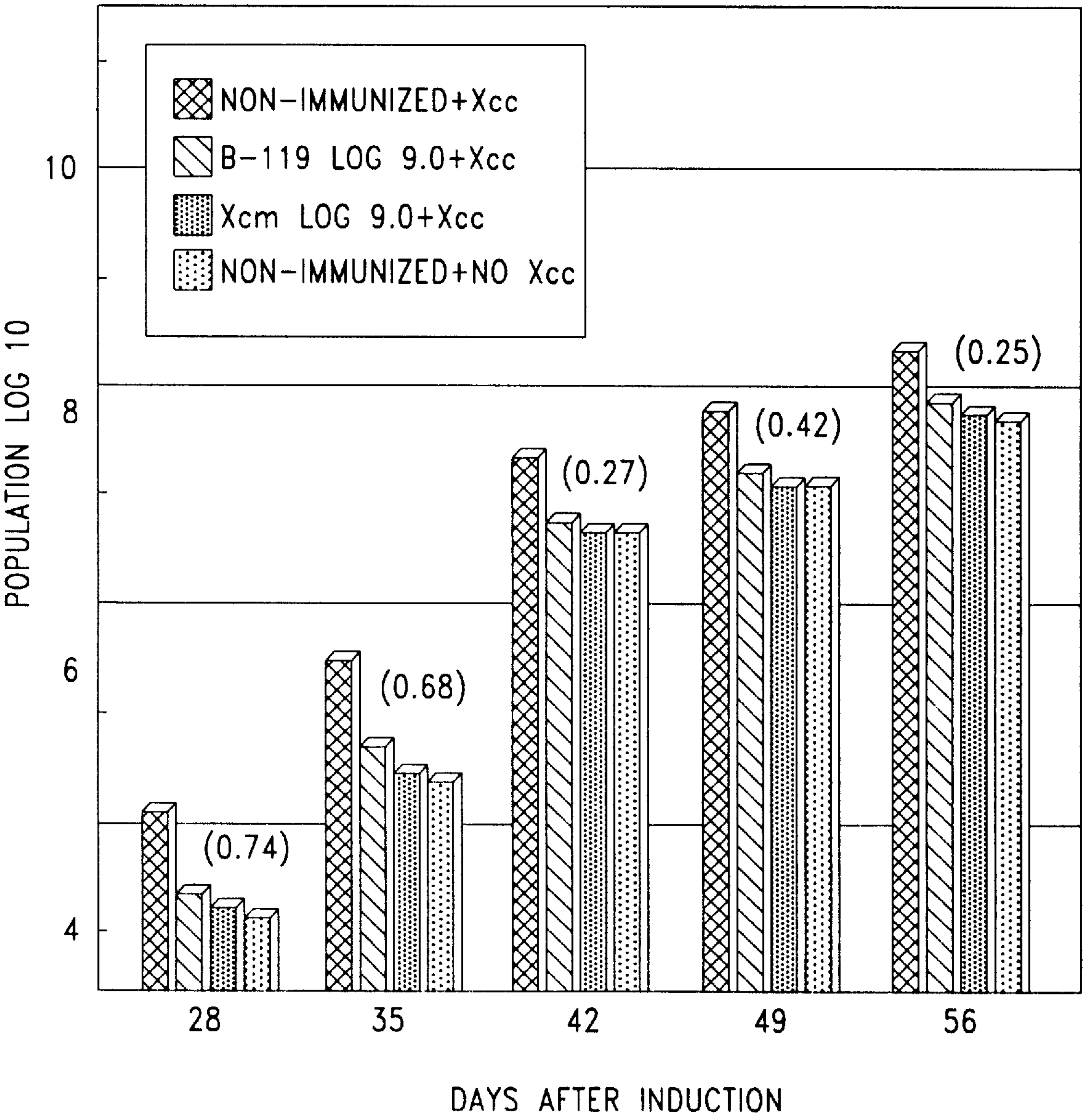
FIG. 12 shows the mean population of pathogenic Xcc after challenge in cabbage leaves induced 21 days earlier with either WXcc, Xcm, or nonimmunized cabbages and nonimmunized cabbages infected with natural pathogenic Xcc present in the Fall 1993 field trial.

FIG. 12 shows the mean population of the pathogenic *Xanthomonas campestris* pv. *campestris* (Xcc) after challenge in cabbage leaves induced 21 days earlier with either log 9.0 cfu/ml of the weakly virulent Xcc isolate B-119, log 9.0 cfu/ml of the incompatible pathogen *X. c.* pv. *malvacearum*, or nontreated cabbages and nontreated cabbages infected with natural pathogenic Xcc present in the Fall 1993 field trial. Cabbages were induced at day 0 and challenged at day 21. Numbers in () represent LSD (P=0.01).

Figure 13:
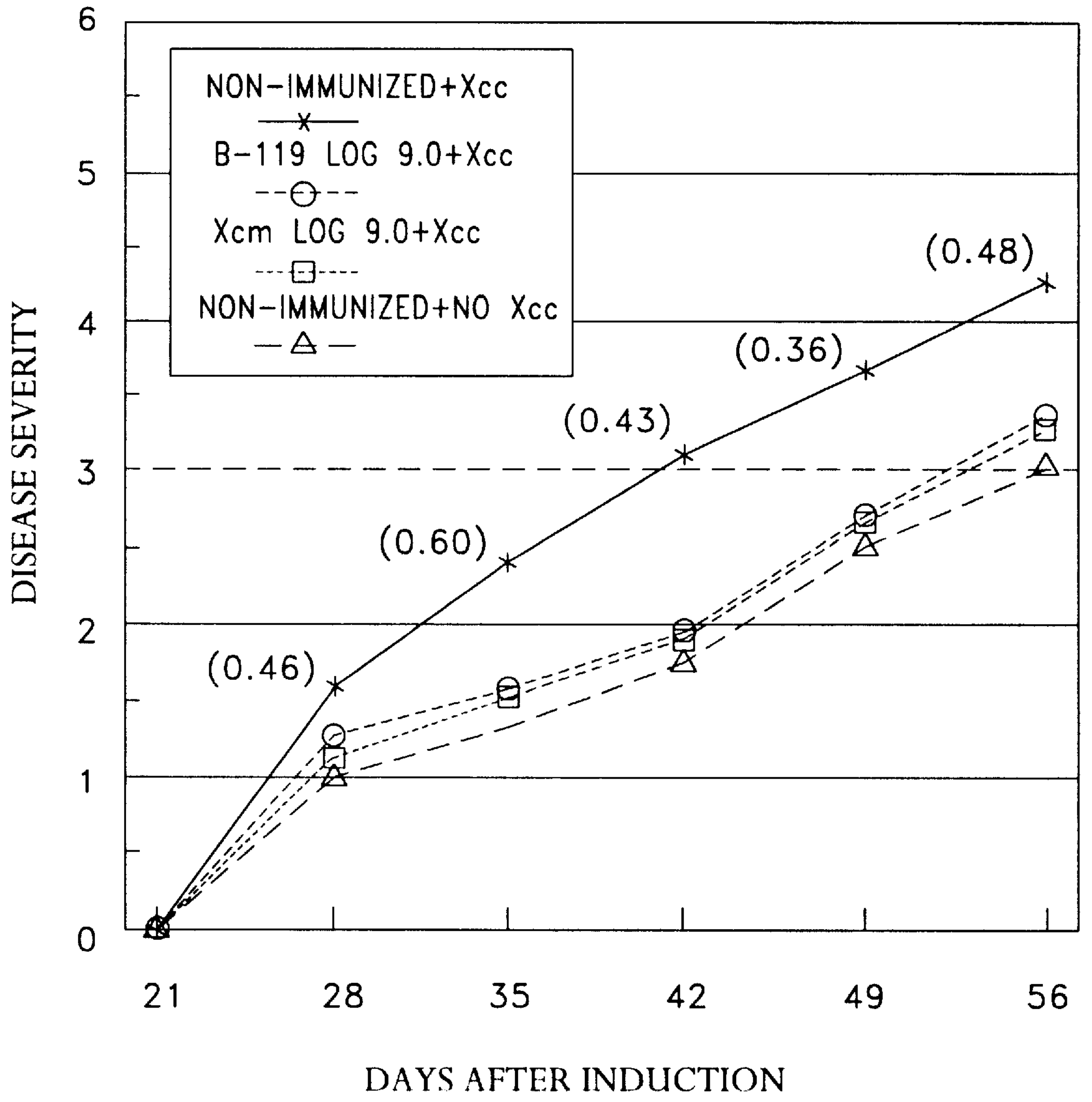
FIG. 13 shows mean disease severity of black rot after challenge with pathogenic Xcc on cabbages induced 21 days earlier with either WXcc, Xcm, or nonimmunized cabbages and nonimmunized cabbages infected with natural pathogenic Xcc present in the Fall 1993 field trial.

FIG. 13 shows mean disease severity of black rot after challenge with pathogenic *Xanthomonas campestris* pv. *campestris* (Xcc) on cabbages induced 21 days earlier with either log 9.0 cfu/ml of the weakly virulent Xcc isolate B-119, log 9.0 cfu/ml of the incompatible pathogen *X. c.* pv. *malvacearum*, or nontreated cabbages and nontreated cabbages infected with natural pathogenic Xcc present in the Fall 1993 field trial. The bold line at level 3.0 represents the economic threshold. Cabbages induced at day 0 and challenged at day 21. Numbers in () represent LSD (P=0.01).

Figure 14A:
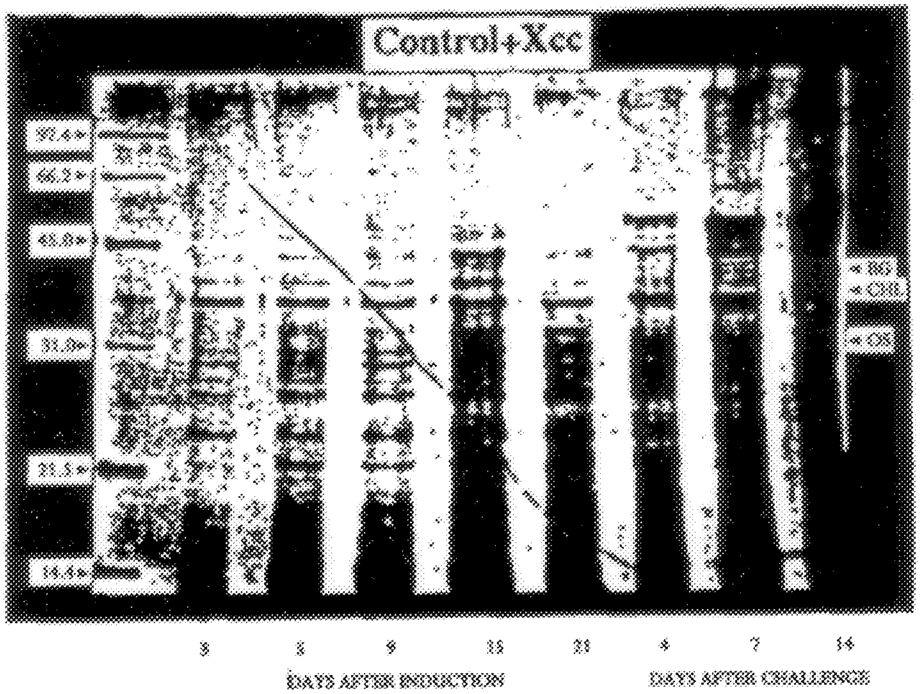
FIG. 14*a* shows sodium dodecyl sulfate-polyacrylamide gel electrophoresis (SDS-PAGE) of proteins in nonimmunized cabbage plants (control).

FIG. 14A shows sodium dodecyl sulfate-polyacrylamide gel electrophoresis (SDS-PAGE) of proteins in nontreated cabbage plants (control). The left lane shows standard proteins and their molecular weights. The next five lanes show proteins prior to challenge with the pathogen *Xanthomonas campestris* pv. *campestris*. The last three lanes show an accumulation of known proteins, including β-1,3-glucanase (BG) (white band, 36.3 kD, Rf=0.440), chitinase/lysozyme2 (CHL2) (dark band below BG, 34.6 kD, Rf=0.460), and osmotin (OS) (26.6 kD, Rf=0.618) and unknown proteins (indicated by arrows) after challenge. Molecular mass markers in kD are given on the right. (Rf=distance of protein from origin distance of dye front from origin.)

Figure 14B:
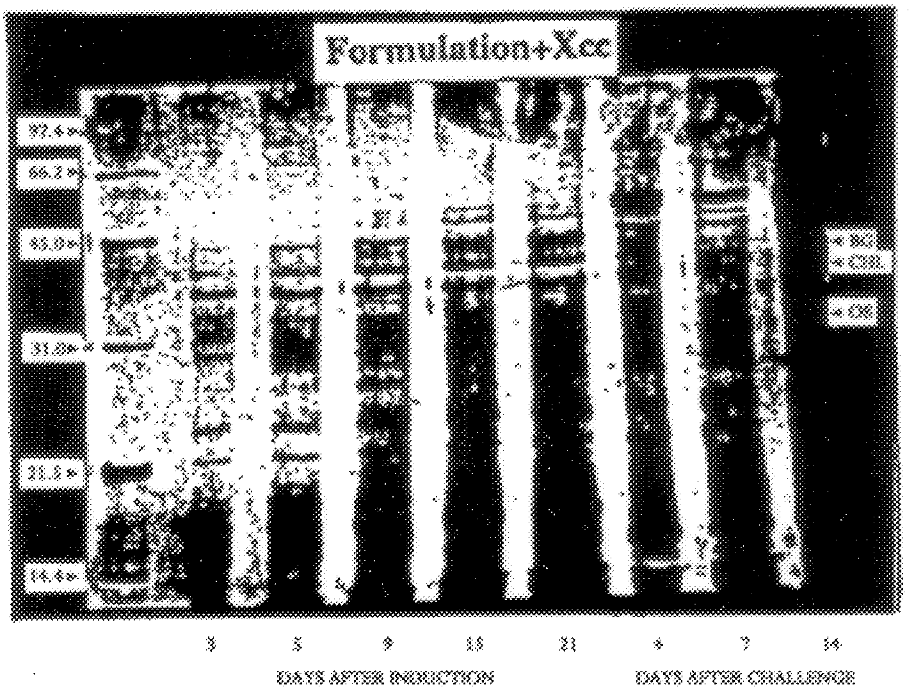
FIG. 14*b* shows sodium dodecyl sulfate-polyacrylamide gel electrophoresis (SDS-PAGE) of proteins in immunized cabbage plants treated with 0.2% surfactant (v/v) alone.

FIG. 14B shows sodium dodecyl sulfate-polyacrylamide gel electrophoresis (SDS-PAGE) of proteins in treated cabbage plants induced with 0.2% surfactant (v/v) plus 0.1M phosphate buffer alone. The left lane shows standard proteins and their molecular weights. The next five lanes show proteins after induction. The last three lanes shown an accumulation of known proteins, including β-1,3-glucanase (BG) (white band, 36.3 kD, Rf=0.440), chitinase/lysozyme2 (CHL2) (dark band below BG, 34.6 kD, Rf=0.460), and osmotin (OS) (26.6 kD, Rf=0.618) and unknown proteins (indicated by arrows) after challenge. Molecular mass markers in kD are given on the right. (Rf=distance of protein from origin÷distance of dye front from origin.)

Figure 14C:
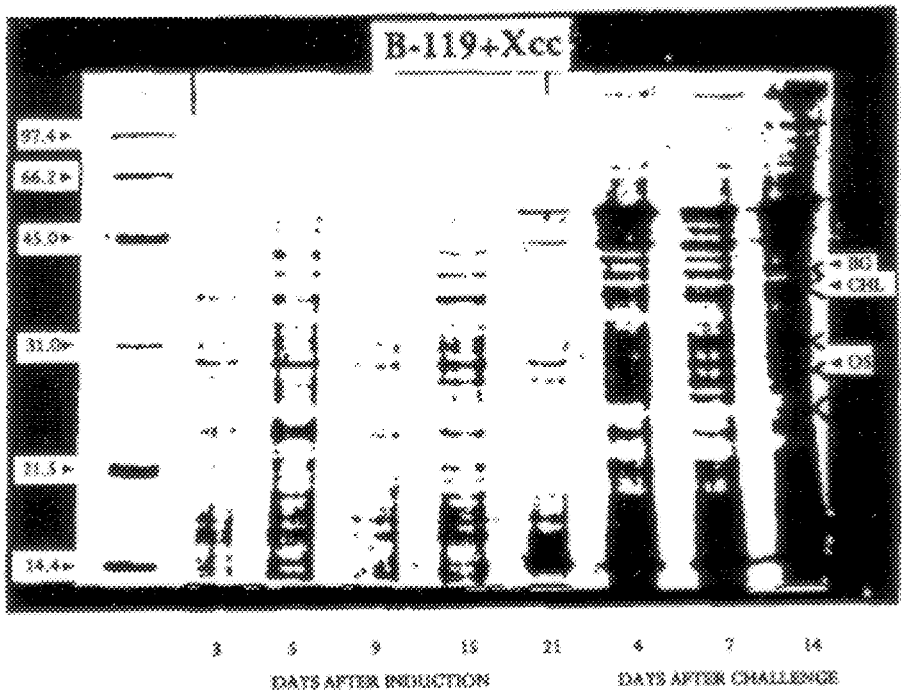
FIG. 14*c* shows sodium dodecyl sulfate-polyacrylamide gel electrophoresis (SDS-PAGE) of proteins in immunized cabbage plants induced with WXcc plus 0.2% surfactant.

FIG. 14C shows sodium dodecyl sulfate-polyacrylamide gel electrophoresis (SDS-PAGE) of proteins in immunized cabbage plants induced with log 9.0 cfu/ml of a weakly virulent *Xanthomonas campestris* pv. *campestris* isolate B-119. The left lane shows standard proteins and their molecular weights. The next five lanes show several proteins after induction. The last three lanes show an accunmulation of known proteins, including β-1,3-glucanase (BG) (white band, 36.3 kD, Rf=0.440), chitinase/lysozyme2 (CHL2) (dark band below BG, 34.6 kD, Rf=0.460), and osmotin (OS) (26.6 kD, Rf=0.618) and unknown proteins (indicated by arrows) after challenge. Molecular mass markers in kD are given on the right. (Rf=distance of protein from origin÷distance of dye front from origin).

Figure 14D:
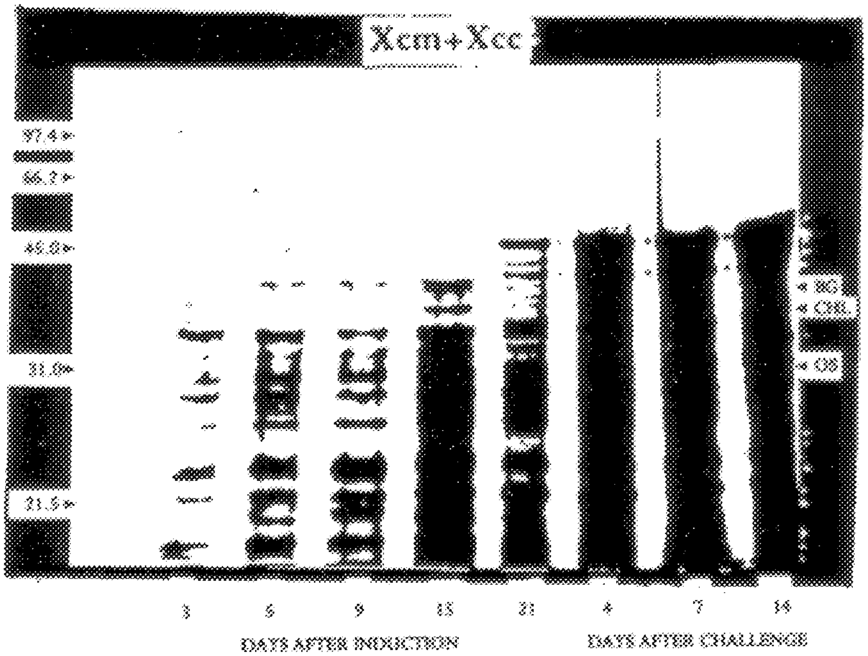
FIG. 14*d* shows sodium dodecyl sulfate-polyacrylamide gel electrophoresis (SDS-PAGE) of proteins in immunized cabbage plants induced with Xcm plus 0.2% surfactant.

FIG. 14D shows sodium dodecyl sulfate-polyacrylamide gel electrophoresis (SDS-PAGE) of proteins in immunized cabbage plants induced with log 9.0 cfu/ml of an incompatible pathogen *Xanthomonas campestris* pv. *malvacearum*. The left side of the picture shows position of proteins and molecular weights. The next five lanes show several proteins after induction. The last three lanes show an accumulation of known proteins, including β-1,3-glucanase (BG) (white band, 36.3 kD, Rf=0.440), chitinase/lysozyme2 (CHL2) (dark band below BG, 34.6 kD, Rf=0.460), and osmotin (OS) (26.6 kD, Rf=0.618) and unknown proteins (indicated by arrows) after challenge. Molecular mass markers in kD are given on the right. (Rf=distance of protein from origin÷distance of dye front from origin.)

DETAILED DESCRIPTION OF THE INVENTION

In a preferred embodiment of the invention, the invention is a method for systemically immunizing plants by topical application of a formulation containing a microorganism which is non-pathogenic or weakly pathogenic for the plant to be immunized and a molecule which promotes the entry of a microorganism into a plant.

Preferably, the molecule is a surfactant which reduces the surface tension on the surface of a plant to a level which permits entry of water into the plant. It is preferred that the surfactant reduce the surface tension of spray droplets on the surface of a plant to below about 30 dynes/cm (30 mNewton/meter), preferably to 28 dynes/cm. Below about 30 dynes/cm, liquids have a zero contact angle on the leaf surface and stomatal flooding occurs.

In a preferred mode, the surfactant may be a nonionic organosilicone surfactant, preferably a trisiloxane, although any suitable surfactant which reduces the surface tension on the surface of a plant to below about 30 dynes/cm can be used to practice the invention. In a preferred mode, the surfactant reduces the surface tension on the surface of a plant to below 25 dynes/cm.

It is preferred that the surfactant, at concentrations used in the formulation of the invention, cause minimal structural damage to microorganisms and to treated plants.

In a preferred mode, the surfactant is polyalkyleneoxide modified polydimethylsiloxane copolymer (Silwet L-77™, Union Carbide, Tarrytown, N.Y.), a nonionic, trisiloxane organosilicone surfactant. The polyalkyleneoxide modified polydimethylsiloxane copolymer surfactant reduces the surface tension on the surface of a plant to 20 dynes/cm. In another preferred embodiment, the surfactant is 2-(3-hydroxypropyl) heptamethyltrisiloxane ethoxylated acetate (Sylgard-309™, Wilbur Ellis, San Francisco, Calif.).

In a preferred embodiment, a non-pathogenic microorganism is used to immunize plants against disease caused by various pathogens. The microorganism may be a bacterium. In cabbage, the non-pathogenic bacteria may be *Xanthomonas campestris* pv. *malvacearum* ("Xcm"), a bacteria which causes angular leaf spot disease in cotton but does not cause disease in cabbage.

Conversely, a weakly pathogenic microorganism may be used to immunize plants against disease caused by various pathogens. The weakly pathogenic microorganism may be an attenuated strain of a pathogenic microorganism which, in the attenuated state, no longer causes significant disease in the target plant. In cabbage, a weakly virulent strain of *Xanthomonas campestris* pv. *campestris* ("WXcc") may be used.

In a preferred embodiment, the formulation contains polyalkyleneoxide modified polydimethylsiloxane copolymer in solution in a buffer solvent. The solvent may be 0.1M potassium phosphate buffer (pH about 7.0), although any suitable buffer which provides an osmotic balance capable of maintaining bacteria may be used. For example, the buffer may contain calcium salts or magnesium salts. The concentration of polyalkyleneoxide modified polydimethylsiloxane copolymer in the buffer is preferably about 0.2% v/v although concentrations higher or lower than 0.2% may be used.

In the preferred embodiment, the non-pathogenic or weakly pathogenic microorganism is in suspension in the buffer/surfactant solution. Higher concentrations of the microorganism in the formulation result in higher levels of immunity. Preferably, when the microorganism is a bacterium, a log 9.0 colony forming units ("cfu")/ml suspension of the microorganism is used, although lower or higher concentrations of bacteria may be used. When the inducing organism is a virus or a fungus, higher concentrations may be feasible or concentrations as high as log 9.0 cfu/ml may not be attainable. Generally, the formulation is aqueous.

The formulation containing the surfactant, the bacteria, and the buffer is applied to the surface of the plant in a single application until the leaves of the plant are partially wetted or wetted. In a preferred embodiment, the formulation is applied by spraying the plants. Applying the formulation in the dark, following a period of dark adaptation, results in fewer "side effects" although the formulation can be applied at any time of day with equally good immunization.

The method of the invention can be practiced, with equally beneficial results, on plants grown in greenhouse conditions and on plants grown in the field. The immunization resulting from the treatment of the invention can be transmissible to plants asexually propagated from immunized plants and to later asexually propagated generations. Resistance to pathogenic infection, following immunization, appears to result from the production of defense proteins in high amounts, including chitinase/lysozyme 2 (CHL2), β-1,3 glucanase (BG), and osmotin (OS).

In a preferred mode, the microorganism is a bacterium which is non-pathogenic to the target plant. Any non-pathogenic bacterium that can be caused to enter the plant and will induce immunity to disease may be used with the method of the invention.

In the examples that follow, various varieties of *Xanthomonas campestris* are used as the immunizing bacterium. *X. campestris* was selected as a model immunizing bacterium because it causes easily recognized disease in plants which can be easily monitored. However, other non-pathogenic bacterium can be used in place of *X. campestris* with equally good results.

Cabbage plants induced with log 9.0 cfu/ml of either WXcc or Xcm had significantly suppressed pathogenic *Xanthomonas campestris* pv. *campestris* ("Xcc") populations throughout the monitoring period as compared to nonimmunized plants. At 56 days post-induction, the plants were beginning to naturally senesce and differences between treatments were smaller, because the pathogen was now overcoming defense mechanisms. In contrast, cabbage plants treated with the formulation not containing immunizing bacteria suppressed Xcc populations only for 3 weeks after challenge. The immunity from the formulation without bacteria probably resulted from the production of low levels of defense proteins due to necrosis (phytotoxicity) caused by surfactant in the stomatal and hydathodal chambers. The levels of defense proteins produced following treatment without immunizing bacteria, however, are insufficient to give long lasting protection to the plant.

The method of the invention results in an effective and efficient immunization of target plants. The formulation is stable at room temperature. Delivery of immunizing microorganisms directly into stomata, hydathodes, and other entry portals of the plant results in long-term, broad based immunity against a variety of pathogens. The method of immunization produces immunity in all types of plants. The immunization results in only a short survival of the inducing agent but long suppression of disease severity and pathogenic microbial populations.

The following examples are merely illustrative of the preferred aspects of the invention and are not to be construed as limiting in any way.

EXAMPLE 1

PREPARATION OF THE FORMULATION

Strain 89-17 of Xcm bacteria, was cultured on a plate containing yeast-extract-dextrose-$CaCO_3$ (YDC) agar at 25° C. for three days. The plate containing the Xcm was then harvested in 9.0 ml sterile potassium phosphate buffer (0.1M, pH 7.0).

The bacteria, at a concentration of log 9.0, were suspended in a solution of 0.2% polyalkyleneoxide modified polydimethylsiloxane copolymer v/v in sterile potassium phosphate buffer (0.1M, pH 7.0).

A second formulation was prepared as described above using the weakly pathogenic organism WXcc (strain B-119 from California), in place of Xcm.

A third formulation, to be used as a non-immunizing control, was prepared as described above but containing no bacteria.

EXAMPLE 2

APPLICATION OF THE FORMULATION

One month old greenhouse grown cabbages of the Round Dutch variety with intermediate susceptibility to black rot disease were induced during the daytime with the formulation containing either Xcm, Wxcc, or no bacteria. The formulation was applied using a hand held aerosol sprayer (Crown power pack, Fisher Scientific, Pittsburgh, Pa.) until leaves were wetted. The cabbage plants were then allowed to grow normally in the greenhouse.

EXAMPLE 3

GROWTH OF NON-PATHOGENIC BACTERIA

Small light brown necrotic lesions were seen at hydathodes in plants induced with the control formulation five days after induction. Dark brown necrotic areas of similar size were seen at hydathodes in the Xcm treated cabbages. Larger dark brown necrotic areas occurred in cabbages induced with WXcc.

Leaf punch samples were collected beyond the zones of necrosis by using a cork borer (1 cm in diam) at 3, 5, 9, 15, and 21 days after induction. The samples were evaluated for population of the inducing organism as follows: Leaf samples were weighed and processed with a stomacher blender (Tekmar, Cincinnati, Ohio) for approximately 3–4 min in a 1:10 dilution (w/v). Samples were serially diluted and plated onto YDC agar and selective SX agar used for isolation of *Xanthomonas campestris* with a spiral plater (Spiral Systems, Inc. Bethesda, Md.). Bacteria were grown at 25° C. for 2 days ON YDC agar and for 4 days ON SX agar.

The population of immunizing bacteria increased through five days after induction, and decreased through 15 days after induction until, at 21 days after induction, the immunizing bacterium could not be detected. See FIGS. 1 and 2.

EXAMPLE 4

CHALLENGE WITH PATHOGENIC ORGANISMS

Twenty one days after induction, cabbage plants were challenged in the dark with 6.0 cfu/ml of pathogenic *Xanthomonas campestris* ("Xcc") formulated and applied as described above for induction. Disease severity of the two immunized groups, the non-immunized control group treated with the formulation containing surfactant but without immunizing bacteria, and a non-treated control group was rated according to the following scale:

0—No damage.

1—Minute necrotic lesion zone (1 to 3 mm in diam) at the hydathodes. No chlorosis around lesion or hydathode.

2—Few small (less than 1 cm in diam) lesions at the leaf edge showing diffuse, ill-defined, chlorotic margin.

3—Several 1.0–2.0 cm in diameter v-shaped lesions with distinct marginal chlorosis and blackened veins within the lesion at older leaves and younger leaves showing necrotic lesions starting systemic disease (the economic threshold).

4—Many large (greater than 2.0 cm in diam), spreading, v-shaped lesions which often coalesced to produce a dried leaf rim.

5—Leaves were badly scorched by coalescing and rapidly expanding lesions.

6—Plant severely stunted and dying.

7—Plant dead.

Samples were collected at 28, 35, 42, 49 and 56 days after induction and level of colonization by the pathogenic Xcc were determined as for the immunizing agents. Data were analyzed as a single contrast comparison with a least significant difference (LSD) using SAS General Linear Model Procedure.

Spray inoculations with the WXcc or with the Xcm resulted in a reduction (P=0.01) of disease severity and also in a reduction of Xcc populations (P=0.01) when plants were challenged 21 days after induction. The cabbage plants immunized with WXcc suppressed the development of Xcc populations (P=0.01) approximately one log unit (10-fold less) at 28 days after induction, a half log unit at 35 and 42 days after induction, and one log unit at 49 days after induction when compared to non-immunized and non-treated plants. See FIG. 3. Plants immunized with Xcm also suppressed the development of Xcc populations (P=0.01) approximately 1.5 log units at 28 and 35 days after induction, and 1.0 log unit at 42 and 49 days after induction, compared to non-immunized and non-treated plants. See FIG. 4. Cabbage plants treated with the formulation control (without immunizing bacteria) suppressed Xcc populations significantly 3 weeks after challenge as compared to non-treated plants. However, there was no difference in Xcc populations between plants treated without immunizing bacteria and non-treated plants at 49 days through the rest of the experiment. At 56 days after induction, differences of Xcc populations among each treatment group were less pronounced.

Immunized cabbage plants with either the WXcc or the Xcm also suppressed development of disease severity significantly (P=0.01), compared to non-immunized plants, throughout the experiment. The non-immunized plants reached the economic threshold (at level 3.0, starting systemic disease) at approximately 42 days after induction and plants treated without immunizing bacteria reached the economic threshold at approximately 45 days after induction. In contrast, cabbage induced with either the WXcc or the Xcm reached the economic threshold at approximately 50 days and 52 days after induction, respectively. Cabbage plants treated with the formulation control had no significant decrease in level of disease severity as compared to non-treated plants at 49 days after induction through the rest of the experiment. See FIGS. 5 and 6. Immunized plants were of marketable quality at 50 days, the optimal harvest date, whereas non-immunized plants greatly exceeded the economic damage threshold at that time.

It was an unexpected observation that the induction of resistance in cabbage was very durable, with disease suppressed throughout the crop season. It had been expected that booster applications would have been needed for season-long protection.

EXAMPLE 5

EFFECT OF DOSE RATE OF BACTERIA

The formulation was prepared as described above using three dose rates of Xcm and WXcc, log 9.0, log 8.0, and log 7.0 cfu/ml in 0.2% polyalkyleneoxide modified polydimethylsiloxane copolymer v/v and 0.1M phosphate buffer. Plants were maintained in greenhouse conditions following induction as described above. The formulation was applied and samples were collected and evaluated as described above prior to challenge with pathogenic bacteria at 3, 5, 9, 15, and 21 days after induction. All plants were challenged with Xcc as described above three weeks after induction. Disease severity and population levels of pathogenic bacteria were evaluated as described above.

In general, the greater the concentration of the inducer, the faster and more effective the induced resistance in the host. Treatments induced with log 8.0 cfu/ml and log 7.0 cfu/ml suppressed black rot disease severity and Xcc populations, but not as well as did induction with log 9.0 cfu/ml of the same organisms. (FIGS. 3 and 4.)

EXAMPLE 6

EFFECT OF CONCENTRATION OF SURFACTANT

The formulation was prepared as described above using log 7.5 cfu/ml of WXcc or Xcm in four concentrations of polyalkyleneoxide modified polydimethylsiloxane copolymer surfactant, 0.1%, 0.15%, 0.2% v/v, and 0.25% in 0.1M phosphate buffer. Plants were maintained in greenhouse conditions following induction as described above. The formulation was applied and samples were collected and evaluated as described above prior to challenge with pathogenic bacteria at 3, 5, 9, 15, and 21 days after induction. All plants were challenged with Xcc as described above three weeks after induction. Disease severity and population levels of pathogenic bacteria were evaluated as described above.

In general, the greater the concentration of surfactant, the greater the penetration of immunizing bacteria into the plants. See FIG. 1. Leaf tissue sampling indicated that populations of WXcc or Xcm within the plant increased with increasing surfactant rates and higher levels of necrotic lesions on cabbage leaves occurred with higher rates of surfactant in the formulation. Necrosis of leaves was considered to be significant only at a concentration of 0.25% surfactant.

EXAMPLE 7

EFFECT OF TIME OF DAY OF INDUCTION

Because stomata gradually close in the dark, the effect of darkness on immunization was evaluated. One month old cabbage were induced as described above with the formulation containing log 9.0 cfu/ml of WXcc or Xcm in 0.2% polyalkyleneoxide modified polydimethylsiloxane copolymer v/v and 0.1M phosphate buffer. The formulation was applied as described above on the plants either during the day or in the dark following at least two hours of darkness.

Immediately following spraying, all cabbages showed darkened water soaked areas due to infiltration of the hydathodes and stomata by the spray solution. The number and area of the water soaked regions was greater in plants treated during the day than in those plants treated in the dark. The water soaked areas were no longer visible after approximately 15 minutes in plants treated in the dark. In those plants treated in the day, the darkened areas persisted for longer periods of time (20–40 min).

In addition, the necrosis seen following application of the formulation containing WXcc was much less severe in those plants treated during the dark. Necrotic lesions were small and only occurred around hydathodes in Xcm induced cabbages, both for cabbages treated during the dark and for those treated during the day.

No difference in Xcc populations or in disease severity was detectable in the plants treated in the dark and the plants treated during the day.

EXAMPLE 8

IMMUNIZATION IN FIELD GROWN PLANTS

The formulation was prepared as described above using log 9.0 cfu/ml of Xcm and WXcc and without immunizing bacteria in 0.2% polyalkyleneoxide modified polydimethylsiloxane copolymer v/v and 0.1M phosphate buffer. Cabbage transplants were grown in the greenhouse during Spring and sprayed with inducing treatments when they were one-month old. Plants were kept in the dark for at least 2 hours just prior to induction. The formulation was then applied as described above.

One week after induction, all cabbage plants were transplanted to the field at Auburn University's E. V. Smith Research Center in Tallassee, Ala. Plots were in single rows 2.0 m apart and 30 cm spaces between individual plants (7 plants/plot). Dipel (1.12 kg/ha) was applied to control cabbage loopers when they appeared. Lannate was occasionally applied as needed, depending upon the appearance of larvae. Fertilizers (Calcium Nitrate and Triple Superphosphate) were applied before seedlings transplanted and were applied once a week in irrigation water (total rate N=67.3 kg/ha, P=67.3 kg/ha, K=0 kg).

Leaf punch samples were collected and evaluated as described above prior to challenge with pathogenic bacteria at 3, 5, 9, 15, and 21 days after induction. All plants were challenged with Xcc at night as described above three weeks after induction. Disease severity and population levels of pathogenic bacteria were evaluated as described above.

The same procedure was conducted at the same location (different field) during the Fall season. Procedures of collection of the samples, determination of inducing bacteria and pathogenic Xcc populations in cabbage leaves, evaluation of disease severity and statistical analysis were the same as in the Spring trial.

Populations of WXcc and Xcm increased through 5 days after induction following which they decreased through 21 days. At 21 days after induction, both WXcc and Xcm were undetectable in cabbage leaf samples. See FIGS. 7 and 11. For both the Spring and Fall cabbage tests, plants immunized with either WXcc or Xcm suppressed both pathogenic Xcc populations and disease severity significantly (P=0.01) throughout the season as compared to non-immunized plants. In the Spring experiment, cabbage plants induced with either WXcc or Xcm suppressed pathogenic Xcc populations (P=0.01) at least one log units (10-fold less) at both 28 and 35 days, and 0.5 log units at 42 days, and again 1.0 log units at 49 days after induction as compared to non-immunized plants.

Cabbage plants sprayed with the formulation without immunizing bacteria also suppressed (P=0.01) pathogenic Xcc populations significantly from 28 to 42 days after induction as compared to non-treated plants, however at lesser levels than those immunized with bacteria. See FIG. 8. Both WXcc and Xcm suppressed development of pathogenic Xcc populations better than the formulation without immunizing bacteria from 35–49 days after induction (14 days after challenge through harvest maturity at 49 days after induction).

Disease severity on non-treated cabbages and non-immunized treated with the formulation without immunizing bacteria progressed very rapidly. See FIGS. 9A and 9B. Non-treated cabbages reached the economic threshold (level 3.0, initial symptoms of systemic disease) approximately 33 days after induction while cabbages treated with the formulation without immunizing bacteria reached the economic threshold at approximately 41 days after induction. In contrast, disease severity of cabbage plants immunized with either WXcc or Xcm progressed much slower not reaching the economic threshold until approximately 50 days after induction which was coincidental with harvest maturity. See FIGS. 9C, 9D, and 10).

In the Fall experiment, cabbage plants induced with either WXcc or Xcm also suppressed the development of pathogenic Xcc populations significantly (P=0.01) at least 1.0 log units (10-fold less) at both 28 and 35 days after induction, and 0.5 log units (5-fold less) at 42 days after induction through the season as compared to non-immunized plants challenged later with pathogenic Xcc.

Black rot disease in the Fall experiment progressed slowly as compared to the Spring experiment. Head formation on cabbage plants in the Fall experiment was also slower than cabbages in the Spring experiment. Non-immunized cabbage plants challenged at 21 days after induction with pathogenic Xcc reached the economic threshold at approximately 40 days after induction. In contrast, cabbage plants induced with inducing bacteria and challenged later with pathogenic Xcc reached the economic threshold approximately 53 days after induction. See FIG. 12.

EXAMPLE 9

IMMUNIZATION OF CUCURBITS

The formulation was prepared as described in Examples 1–3 using *Xanthomonas campestris* pv. *malvacearum* as the inducing bacteria. The formulation was applied as described above by spraying 2–3 week old cucumber seedlings grown in the field. Cucumber plants sprayed with inducing treatments had reduced disease developed compared to controls upon infection with *Erwinia tracheiphila*.

Similar results are expected upon immunization of other cucurbits, such as squash, watermelon, and muskmelon, using endophytic bacteria or other non-pathogenic bacteria, as described above.

EXAMPLE 10

IMMUNIZATION IN CEREAL PLANTS

The formulation is prepared as described above in Examples 1–3 using Xcm as the immunizing microorganism. The formulation is applied as described above by spraying rice plants. The formulation can likewise be applied to other cereals, such as barley, corn, oat, and wheat.

As compared to control non-treated and control non-immunized rice plants, the immunized plants have reduced lesion formation and reduced populations of pathogenic organisms when challenged 21 days after induction. The immunity lasts throughout the growing season.

EXAMPLE 11

IMMUNIZATION IN SOLANACEOUS PLANTS

The formulation was prepared as described above in Example 1 using Xcm as the immunizing bacteria and was applied to tomato plants by spraying until leaves were wetted. The leaves of the tomatoes were examined as described above at days 5, 7, 9, 15, and 21 after induction, at which time they were challenged with a pathogenic strain of *Xanthomonas campestris* pv. *vesicatoria*.

The treated tomatoes were found to have decreased populations of the pathogenic bacteria and decreased severity of disease (bacterial spot) when compared to non-treated control tomato plants and to tomato plants treated with the formulation lacking the immunizing bacteria.

Similar results are expected to be achieved with immunization of other solanaceous plants such as pepper and potato.

EXAMPLE 12

IMMUNIZATION OF LEGUMES

The formulation is prepared as described above using Xcm as the immunizing bacteria. Soybeans treated with the formulation have decreased growth of pathogenic bacteria and decreased symptoms of disease compared to non-immunized soybean plants. Other legumes that are expected to develop immunity following treatment include beans, cowpea, and pea.

EXAMPLE 13

IMMUNIZATION OF FRUIT TREES

The formulation is prepared as described above using Xcm as the immunizing bacteria. Pear trees treated with the formulation have decreased growth of pathogenic bacteria and decreased symptoms of disease compared to non-immunized pear trees. Other fruit trees that are expected to develop immunity following treatment include grape, peach, plum, apple, and citrus fruits.

EXAMPLE 14

IMMUNIZATION OF FORESTRY TREES

The formulation is prepared as described above using Xcm as the immunizing bacteria. Douglas fir trees treated with the formulation have decreased growth of pathogenic bacteria and decreased symptoms of disease compared to non-immunized trees. Other conifers, such as pine trees, are expected to develop similar immunity following treatment.

EXAMPLE 15

IMMUNIZATION OF ORNAMENTAL PLANTS

The formulation is prepared as described above using Xcm as the immunizing bacteria. Carnation plants treated with the formulation have decreased growth of pathogenic bacteria and decreased symptoms of disease compared to non-immunized carnations. Other ornamental plants, such as roses, are expected to develop similar immunity following treatment.

EXAMPLE 16

IMMUNIZATION OF COTTON

The formulation is prepared as described above using pathogenic Xcc as the immunizing bacteria. Cotton plants treated with the formulation have decreased growth of pathogenic bacteria and decreased symptoms of disease compared to non-immunized cottons.

EXAMPLE 17

IMMUNIZATION OF OTHER PLANTS

The formulation is prepared as described above using Xcm as the immunizing bacteria. Tobacco, beet, coffee, and radish plants treated with the formulation have decreased growth of pathogenic bacteria and decreased symptoms of disease compared to non-immunized carnations. Other ornamental plants, such as roses, are expected to develop similar immunity following treatment.

EXAMPLE 18

METHODS OF ASSESSING RESISTANCE FOLLOWING IMMUNIZATION

The formulation was prepared as described above using Xcm and WXcc at a dose rate of log 9.0 cfu/ml in 0.2% polyalkyleneoxide modified polydimethylsiloxane copolymer v/v and 0.1M phosphate buffer. Four treatment groups were established: 1) non-treated cabbage plants, 2) cabbage plants treated with the formulation not containing immunizing bacteria, 3) cabbage plants treated with the formulation containing Xcm, and 4) cabbage plants treated with the formulation containing WXcc. Plants were treated at one month of age in greenhouse conditions and were transplanted outdoors one week later. At 21 days following induction, all plants were challenged with log 6.0 cfu/ml of pathogenic Xcc as described above.

Two to three replication leaf punch samples (1.0 cm) were collected from each plant in each replication from each treatment group. Samples were collected from the youngest symptomatic leaves beyond the zone of symptoms by using a cork borer at 3, 5, 9, and 21 days after induction and at 4, 7, and 14 days after challenge. Leaf samples from each treatment group were pooled and frozen in liquid $N_2$ and crushed into a fine powder in a mortar and pestle. Sea sand (1:1 w/w) and 0.05M sodium acetate buffer (pH 6.0, 1:3 w/v) were added into the mortar.

Samples were ground until homogenized and the homogenate was centrifuged at 6,000 g for 15 minutes in a Sorvall (RC5C) centrifuge (DuPont Co., Wilmington, Del.) equipped with a HB-4 swinging bucket rotor. The supernatant was retained and recentrifuged in a Hermle microcentrifuge (National Labnet Co., Woodbridge. N.J.) at 4,000 g for 10 minutes. The supernatant was again retained and protein concentrations in the supernatant were determined by using a commercial kit (Bio-Rad, Richmond, Calif.). A colorimetric assay of the proteins was measured in a Perkin-Elmer Lambda 3A spectrophotometer (Perkin-Elmer, Norcross, Ga.) at 595 nm.

The proteins were separated by native polyacrylamide gel electrophoresis. Electrophoresis was performed using 0.5 mm mini slab-gel according to manufacturer specifications (Bio-Rad) by using a 5% stacking gel and a 13% separating gel at 200 volts until the dye band ran out of the bottom of the gel. Proteins were developed by utilizing the Silver stain technique using a commercial kit (Bio-Rad).

The non-treated cabbage plants produced only low levels of defense proteins prior to challenge with pathogenic Xcc. Prior to challenge, the WXcc and Xcc treated plants produced defense proteins in the greatest quantities. The plants treated with the formulation without immunizing bacteria produced proteins in greater quantities than did the non-treated plants, but in lower quantities than did the immunized plants. See FIGS. 14*a*, 14*b*, 14*c*, and 14*d*.

At 4 days after challenge, several new proteins were produced in cabbage plants immunized with either the WXcc or the Xcm. Cabbage plants treated without immunizing bacteria also produced several proteins at 4 days after challenge but in lower quantities than did the WXcc and the Xcm. See FIG. 14*a*. In contrast, the non-treated plants still produced only small quantities of proteins. The non-treated plants, however, began to produce several defense proteins in low quantities 7 days post-challenge, and produced more proteins at 14 days after challenge (FIG. 14*a*).

Cabbage plants immunized with inducing bacteria had an elevated accumulation of eleven proteins including three known ones (β-1,3-glucanase, chitinase/lysozyme2, osmotin) and eight other unknown proteins (indicated by black arrows) from 4 days through 14 days after challenge. Although, cabbage plants treated with surfactant had a degree of increased accumulation of some of these proteins after challenge compared to non-treated controls, the quantities of those proteins were less than cabbage plants immunized with inducing bacteria plus surfactant.

Cabbage plants induced with the Xcm produced proteins in greater quantities than did the WXcc in both pre- and post-challenge. See FIGS. 14*c* & 14*d*.

The invention has been illustrated as described herein, but one skilled in the art can readily provide variations, substitutions, e.g., of the surface active molecule and the inducer microorganisms, and apply the formulation to other plants without departing from the spirit of and the benefits conferred by the invention.

REFERENCES

Adams, A. J., Fenlon, J. S., and Palmer, A. 1988. Improving the biological efficacy of small droplets of permathrin by the addition of silicon-based surfactants. Ann. Appl. Biol. 122:19–31.

Agrios, G. N. 1989. Plant Pathology ($3^{rd}$ Edition). Academic Press, New York.

Aitken-Christie, J., and Coker, A. 1986. Surfactants aid uptake of cytokinin and urea into juvenile *Pinus radiata* plantlets. Int. Plant Propagators. Soc. Combined Proc. 36:499–506.

Aist, J. 1983. Structure responses as resistance mechanisms. In: *The dynamics of Host Defense* (J. Bailey and B. Deverall, eds.). Academic, New York, pp. 33–70.

Bishop, N. J., and Field, R. J. 1983. Improved performance of glyphosate in the full season control of perennial ryegrass. Aspects Appl. Biol. 4:363–370.

Buick, et al. 1993. The Role of surface Tension of Spreading Droplets in Absorption of a Herbicide Formulation via Leaf Stomata. Pestic. Sci. 38:227–235.

Caruso, F., and J. Kuć, 1979. Induced resistance of cucumber to anthracnose and angular leaf spot by *Pseudomonas lachrymans* and *Colletotrichum lagenarium*. Physiol. Plant Pathol. 14:191–201.

Chai, H. B., and Doke, N. 1987. Systemic activation of $O_2$ generating reaction, superoxide dismutase, and peroxidase in potato plants in relation to induction of systemic resistance to *Phytophthora infestans*. Ann. Phytopathol. Soc. JPN 53:585–590.

Cloud, A. M. E., and Deverall, B. J. 1987. Induction and expression of systemic resistance to the anthracnose disease in bean. Plant Pathology 36:551–557.

Davis, K., G. Lyon, A. Darvill, and P. Albersheim, 1982. A polygalacturonic acid lyase isolated from *Erwinia carotovora* is an elicitor of phytoalexins in soybeans. Plant Physiol., (Suppl.) 69:142.

Dehne, H. W., Stenzel, K., and Schonbeck, F. 1984. The efficiency of induced resistance under practical culture conditions. III Reproduction of powdery mildew on induced resistant plants. Plant Dis. Prot. 91:258–265.

Dean, R. A., and J. Kuć, 1985. Induced systemic protection in plants. Trends in Biotechnology 3:125–129.

Dean, R. and J. Kuć, 1986a. Induced systemic protection in cucumber: the source of the signal. Physiol. and Mol. Plant Pathol. 28:227–233.

Dean, R. and J. Kuć, 1986b. Induced systemic protection in cucumber: effect of inoculum density on symptom development of *Colletotrichum lagenarium* in protected and unprotected plants. Phytopathology 76:186–189.

Deverall, B. 1982. Introduction. In: *Phytoalexins* (J. Bailey and J. Mansfield, eds.). Blackie and Sons, Glagow, pp. 1–20.

Dodson, KM (see references in disclosure document)

Field, R. J., and Bishop, N. G. 1988. Promotion of stomatal infiltration of glycosate by an organosilicone surfactant reduces the critical rainfall period. Pestic. Sci. 24:55–62.

Giri, D. N., and Sinha, A. K. 1979. Effect of nontoxic chemical on brown spot disease in rice seedlings. Int. Rice Res. Newsl. 4:10–11.

Gottstein, H. D., and Kuć, J. 1989. Induction of systemic resistance in cucumber by phosphates. Phytopathology 79:176–179.

Greenberg, J., Monselise, S. P., and Goldschmidt, E. E. 1987. Improvement of gibberellin efficiency in prolonging the citrus harvest season by the surfactant L-77. J. Am. Soc. Hort. Sci. J. 112:625–629.

Hammerschmidt, R., and J. Kuć, 1982. Lignification as a mechanism for induced systemic resistance in cucumber. Physiol. Plant Pathol. 20:61–71.

Hildebrand, P. D. 1989. Surfactant-like characteristics and identity of bacteria associated with broccoli head rot in Atlantic Canada. Can. J. Plant pathol. 11:205–214.

Hoitink, H. A. J., and Fahy, P. C. 1986. Basis for the control of soil-borne plant pathogens with composts. Annu. Rev. Phytopathol. 24:93–114.

Karban, R., and J. Carey, 1984. Induced resistance of cotton seedlings to mites. Science 225:53–54.

Kuć, J., and F. Caruso, 1977. Activation coordinated chemical defense against disease in plants. In: *Host Resistance To Pests* (P. Hedin, ed.). American Chemical Society Press, Washington, D.C., pp. 78–89.

Kuć, J. 1982a. Phytoalexins from the Solanaceae. In: *Phytoalexins* (J. Bailey and J. Mansfield, eds.). Blackie and Sons, Glasgow, pp. 81–105.

Kuć, J. 1982b. Induced immunity to plant disease.
Bioscience 32:854–860.

Kuć, J. 1982c. The immunization of cucurbits against fungal, bacterial and viral diseases. In: *Plant Infection.* The Physiological and Biochemical Basis, ed. by Y. Asada, W. R. Bushnell, S. Ouchi & C. P. Vance, pp. 137–155. Japanese Science Society Press, Tokyo.

Kuć, J., and C. Preisig, 1984. Fungal regulation of disease resistance mechanisms in plants. Mycologia 76(5) :767–784.

Kuć, J. 1985a. Expression of latent genetic information for disease resistance in plants. In: *Cellular and Molecular Biology of Plant Adaptation*, pp. 100–118. Foundation 102. Pitman, London.

Kuć, J., and J. Rush, 1985b. Phytoalexins. Arch. Biophys. 236:379–389.

Kuć, J. 1987. Plant immunization and its applicability for disease control. In: *Innovative Approaches to Plant Disease Control*, J. Chet (ed.). John Willey, New York, pp. 255–274.

Mauch, F., Hadwiger, L. A., and Boller, T. 1988. Antifungal hydrolases in pea tissue. Purification and characterization of two chitinases and two β-1,3-glucanases differentially regulated during development and in response to fungal infection. Plant Physiol. 87:325–333.

Mauch, F., Mauch-Mani, B., and Boller, T. 1988. Antifungal hydrolases in pea tissue. II Inhibition of fungal growth by combinations of chitinases and 1,3-β-glucanases. Plant Physiol. 88:929–942.

McIntyre, J., J. Kuc, and E. Williams, 1975. Protection of Bartlett pear against fireblight with deoxyribonucleic acid from virulent and avirulent *Erwinia amylovora*. Physiol. Pathol. 7:153–170.

Neumann, P. M., and Prinz, R. 1974. Evaluation of surfactants for use in the spray treatment of iron chlorosis in citrus tree. J. Sci. Food Agric. 25:221–226.

Nothnagel, E., M. McNeil, P. Albersheim, and A. Dell, 1983. Host-pathogen interactions XXII. A galacturonic acid oligosaccharide from plant cell walls elicits phytoalexins. Plant Physiol. 71:916–926.

Peer, R. V., G. J. Niemann, and B. Schippers, 1991. Induced resistance and phytoalexin accumulation in biological control of Fusarium wilt of carnation by *Pseudomonas sp.* strain WCS417r. Phytopathology 81:728–733.

Richmond, S., J. Kuć, and J. Elliston, 1979. Penetration of cucumber leaves by *Colletotrichum lagenarium* is reduced in plants systemically protected by previous infection with the pathogen. Physiol. Plant Pathol. 14:329–338.

Roggenbuck, et al. 1993. Study of Enhancement of Herbicide Activity an dRainfastness by an Organosilicone Adjuvant Utilizing Radiolabelled Herbicide and Adjuvant. Pestic. Sci. 37:121–125

Salt, S. D., Tuzun, S., and Kuć, J. 1986. Effect of β-ionone and abscisic acid on the growth of tobacco and resistance to blue mold. Mimicry of effects of stem infection by *Peronospora tabacina* Adam. Physiol. and Mol. Plant Pathol. 28:287–297.

SAS Institute, 1988. "SAS/Stat User's Guide, Statistics" Release 6.03, SAS Institute, Cary, N.C.

Sequeira, L. 1983. Mechanisms of induced resistance in plants. Annu. Rev. Microbiol. 37:51–79.

Smith, D. 1982. Toxicity of Phytoalexins. In: *Phytoalexins* (J. Bailey and J. Mansfield, eds.). Blackie and Sons, Glasgow, pp. 218–252.

Singh, Megh. 1993. Effect of Organosilicon-Based Adjuvants on Herbicide Efficacy. Pestic. Sci. 38:219–225.

Smith, J., and Hammerschmidt, R. 1988. Comparative study of acidic peroxidases associated with induced resistance in cucumber, muskmelon and watermelon. Physiol. and Mol. Plant Pathol. 33:255–261.

Stevens, Peter J. G. 1993. Organosilicone Surfactants as Adjuvants for Agrochemicals. Pestic. Sci. 38:103–122.

Stock, David. 1993. Possible Mechanisms for Surfactants-Induced Foliar Uptake of Agrochemicals. Pestic. Sci. 38:165–177.

Stolle, K., Zook, M., Shain, L., Hebard, F. and Kuć, J. 1988. Restricted colonization by *Peronospora tabacina* and phytoalexin accumulation in immunized tobacco leaves. Phytopathology 78:1193–1197.

Templeton, G. E. 1982. Status of weed control with plant pathogens. In: *Biological Control of Weeds with Plant Pathogens* (R. Charudattan and H. L. Walker. Eds.). pp. 29–44. Wiley, New York.

Tuzun, S., W. Nesmith, and J. Kuć, 1984. The effect of stem infections with Peronospora tabacina and metalaxyl treatment on growth of tobacco and protection against blue mold in the field. Phytopathology 76:804 (Abstract).

Tuzun, S., and J. Kuć, 1985a. Movement of a factor in tobacco infected with *Peronospora tabacina* Adam which systemically protects against blue mold. Physiol. Plant Pathol. 26:321–330.

Tuzun, S. and Kuć, J. 1987. Persistence of induced/systemic resistance to blue mold in tobacco plants derived via tissue culture. Phytopathology 77:1032–1035.

Tuzun, S. and Kuć, J. 1991. Plant Immunication: An Alternative to Pesticides for Control of Plant Diseases in the Greenhouse and Field. *Food and Fertilizer Technology Center*, Technical Bulletin, No. 124.

Uknes, et al., 1993. The Molecular Biology of Systemic Acquired Resistance. In: *Plant Responses to the Environment*, ed. by Peter M. Gresshoff, pp. 1–9. CRC Press.

Wei, G., Kloepper, J. W., and Tuzun, S. 1991. Induction of systemic resistance of cucumber to *Colletotrichum orbiculare* by select strains of plant growth-promoting rhizobacteria. Phytopathology 81:1508–1512.

Wessels, J. G. H. 1986. Cell wall synthesis in apical hypha. Int. Rev. Cytol. 104:37–79.

Williams, P. H., T. Staub, and J. C. Sutton, 1971. Inheritance of resistance in cabbage to black rot. Phytopathology 62:247–252.

Wood, R. K. S. 1982. Active Defense Mechanisms of Plants. Plenum, New York.

Van Loon, L. C. 1982. Regulation of changes in proteins and enzymes associated with active defense against virus infection. In: *Active Defense Mechanisms in Plants*, Ed. by R. K. S. Wood, pp. 247–273. Plenum, New York.

Vögeli, U., Meins, F. Jr., and Boller, T. 1988. Co-ordinated regulation of chitinase and β-1,3-glucanase in bean leaves. Planta 174:364–372.

Zidak, N. K., P. A. Backman, and J. J. Shaw, 1992. Promotion of bacterial infection of leaves by an organosilicone surfactant: Implications for biological weed control. Biological Control 2: 111–117.

What is claimed is:

1. A biologically active systemic immunity-inducing formulation for applying, without wounding, to the surface of a part of a live target plant which plant has natural openings Oselected from the group consisting of stomates, hydathodes, nectaries, and lenticles, to induce non-specific systemic resistance to a pathogen of the plant by controlling the development of disease due to the pathogen, which formulation comprises a concentration effective to promote non-specific systemic resistance against pathogens of a suspension of a microorganism which is not pathogenic to the target plant, which microorganism will propagate within the plant to reach a peak population within the plant, which population drops to a substantially zero by 21 days following application of the formulation, and a surfactant in a concentration which reduces the surface tension on the surface of the part of the target plant below about 30 dynes/cm, at which level of surface tension the contact angle of liquids on the surface is zero and flooding of stomata, hydathodes, and other plant entry portals occurs, and which promotes penetration of the microorganism into thte plant, and which formulation causes the formation of defense immunity imparting proteins within the target plant.

2. The formulation of claim 1 wherein the surfactant is a nonionic polysilicone surfactant.

3. The formulation of claim 2 wherein the surfactant is selected from the group consisting of a polyalkyleneoxide modified polydimethylsiloxane copolymer having the formula

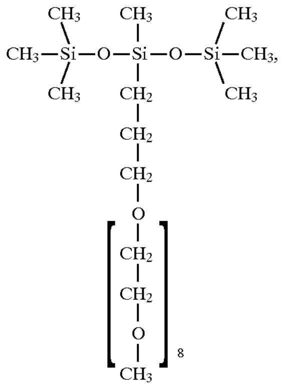

and 2-(3-hydroxypropyl) heptamethyltrisiloxane ethoxylated acetate.

4. The formulation of claim 3 wherein the microorganism is a bacterium which is naturally not pathogenic to the target plant.

5. The formulation of claim 4 wherein the immunizing bacterium is *Xanthomonas campestris* pv. *malvacearum.*

6. The formulation of claim 5 wherein the target plant is selected from the group consisting of cucurbits, solanaceous plants, and Brassica.

7. The formulation of claim 6 wherein the target plant is selected from the group consisting of cabbage, cucumber, and tomato.

8. The formulation of claim 3 wherein the microorganism is an attenuated strain of a bacterium which is a pathogen of the target plant.

9. The formulation of claim 6 wherein the bacterium is *Xanthomonas campestris* pv. *campestris.*

10. The formulation of claim 9 wherein the target plant is selected from the group consisting of cucurbits, solanaceous plants, and Brassica.

11. The formulation of claim 10 wherein the target plant is selected from the group consisting of cabbage, cucumber, and tomato.

12. A method of systemically inducing a resistance to a pathogen in a live plant which has natural openings selected from the group consisting of stomates, hydathodes, nectaries, and lenticels, and is capable of being induced to produce systemic immunity, comprising applying, without wounding, to the surface of a part of the plant a formulation comprising a concentration effective to promote non-specific systemic resistance against pathogens of a suspension of a microorganism which is not pathogenic to the target plant, which microorganism will propagate within the plant to reach a peak population within the plant, which population drops to substantially zero by 21 days following application of the formulation, and a surfactant in a concentration which reduces the surface tension on the surface of the part of the target plant to a level at which liquids have a zero contact angle on the surface and flooding of stomata, hydathodes, and other plant entry portals occurs to promote penetration of the microorganism into the plant, inducing non-specific systemic resistance to pathogens, and forming defense proteins against the pathogen within the target plant.

13. The method of claim 12 wherein the defense proteins are formed before onset of disease due to the pathogen.

14. The method of claim 13 wherein the surfactant is a nonionic polysilicone surfactant which reduces the surface tension to a value below which the contact angle of water is zero.

15. The method of claim 14 wherein the surfactant is selected from the group consisting of a polyalkyleneoxide modified polydimethylsiloxane copolymer having the formula

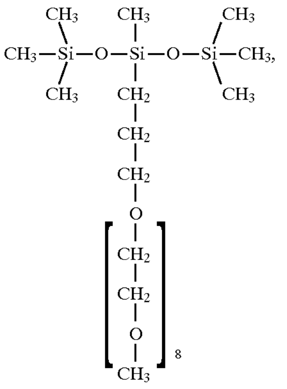

and 2-(3-hydroxypropyl) heptamethyltrisiloxane ethoxylated acetate.

16. The method of claim 15 which further comprises causing the plant having induced resistance to the pathogen to grow to maturity.

17. The method of claim 16 wherein the microorganism is a bacterium which is naturally not pathogenic to the target plant or which is an attenuated strain of a bacterium which is a pathogen to the target plant.

18. The method of claim 17 wherein the naturally non-pathogenic bacterium is *Xanthomonas campestris* pv. *malvacearum* and wherein the attenuated strain is *Xanthomonas campestris* pv. *campestris*.

19. The method of claim 13 wherein the microorganism which penetrates the plant dies after an initial period of growth in the plant.

20. The method of claim 19 wherein the target plant is selected from the group consisting of cucurbits, solanaceous plants, and Brassica.

21. The method of claim 20 wherein the target plant is selected from the group consisting of cabbage, cucumber, and tomato.

22. The method of claim 16 which further comprises applying to the surface of the plant a booster application of the formulation subsequently to the initial application, thereby inducing season-long resistance to the pathogen.

23. The formulation of claim 3 wherein the surfactant is a polyalkyleneoxide modified polydimethylsiloxane copolymer having the formula

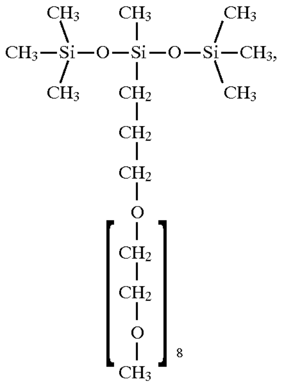

in a concentration of from about 0.1 to 0.25% v/v.

24. The formulation of claim 1 wherein the concentration of microorganism is between about log 7.0 and log 9.0 colony forming units per ml.

25. The formulation of claim 1 wherein the surface of the target plant contains stomates, hydathodes, nectaries and/or lenticels.

26. The formulation of claim 1 wherein the microorganism is a virus bacterium, or a fungus.

27. The method of claim 15 wherein the surfactant is a polyalkyleneoxide modified polydimethylsiloxane copolymer having the formula

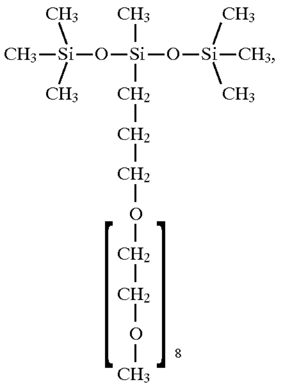

in a concentration of from about 0.1 to 0.25% v/v.

28. The method of claim 12 wherein the concentration of microorganism is between about log 7.0 and log 9.0 colony forming units per ml.

29. The method of claim 12 wherein the surface of the target plant contains stomates, hydathodes, nectaries and/or lenticels.

30. The method of claim 12 wherein the microorganism is a virus, bacterium, or a fungus.

31. The formulation of claim 1 wherein the concentration of the surfactant is less than that which causes significant necrosis to the plant.

32. The method of claim 12 wherein the concentration of the surfactant is less than that which causes significant necrosis to the plant.

33. The formulation of claim 1 wherein the defense protein are formed before the onset of disease due to the pathogen.

34. The formulation of claim 1 wherein the defense proteins are selected from the group consisting of osmotin, hydrolytic enzymes, and peroxidases.

35. The formulation of claim 34 wherein the hydrolytic enzymes are selected from the group consisting of chitinase/lysozyme and β-1,3-glucanase.

36. The formulation of claim 1 wherein the immunity lasts until harvest time of the immunized plant.

37. The formulation of claim 1 wherein the peak population of the microorganism is at 5 days following application of the formulation.

38. The method of claim 12 wherein the defense proteins are formed before the onset of disease due to the pathogen.

39. The method of claim 12 wherein the defense proteins are selected from the group consisting of osmotin, hydrolytic enzymes, and peroxidases.

40. The method of claim 39 wherein the hydrolytic enzymes are selected from the group consisting of chitinase/lysozyme and β-1,3-glucanase.

41. The method of claim 12 wherein the immunity lasts until harvest time of the immunized plant.

42. The method of claim 12 wherein the peak population of the microorganism is at 5 days following application of the formulation.

43. A non-specific systemic immunized live plant treated with a formulation comprising a microorganism which is not pathogenic to the plant in a concentration effective to promote non-specific systemic resistance against pathogens of the plant, which microorganism propagates within the plant and reaches a peak population inside the plant, which population will and drops to substantially zero within 21 days, and a polysilicone surfactant in a concentration effective to reduce the surface tension on the surface of the part of the plant below about 30 dynes/cm, at which level of surface tension the contact angle of liquids on the surface is zero and flooding of stomata, hydathodes, and other plant entry portals occurs.

44. The plant of claim 43 wherein defense proteins are formed before the onset of disease due to the pathogen.

45. The plant of claim 43 in which darkened areas on the surface of the plants are visible due to infiltration of the formulation into hydathodes and stomata of the plant.

46. The plant of claim 43 which is selected from the group consisting of cucurbits, solanaceous plants, and Brassica.

47. The plant of claim 43 which is selected from the group consisting of cabbages, cucumber, and tomato.

48. The plant of claim of 43 wherein the microorganism is an attenuated strain of a bacterium which is a pathogen of the target plant.

49. The plant of claim 43 wherein the surfactant is selected from the group consisting of a polyalkyleneoxide modified polydimethyisiloxane copolymer having the formula

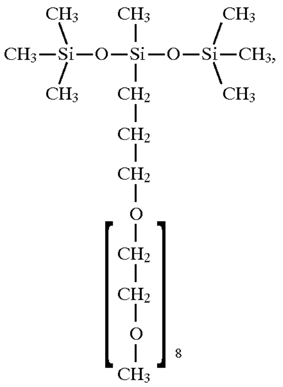

and 2-(3-hydroxypropyl) heptamethyltrisiloxane ethoxylated acetate.

50. The plant of claim 43 wherein the peak population of the microorganism is at 5 days following application of the formulation.

* * * * *